US007465452B2

(12) United States Patent
Itoh

(10) Patent No.: US 7,465,452 B2
(45) Date of Patent: Dec. 16, 2008

(54) TUMOR ANTIGEN

(75) Inventor: Kyogo Itoh, Kiyama-machi (JP)

(73) Assignee: Green Peptide Co., Ltd., Fukuoka (JP)

( * ) Notice: Subject to any disclaimer, the term of this patent is extended or adjusted under 35 U.S.C. 154(b) by 785 days.

(21) Appl. No.: 10/062,257

(22) Filed: Feb. 1, 2002

(65) Prior Publication Data

US 2002/0128201 A1 Sep. 12, 2002

Related U.S. Application Data

(63) Continuation-in-part of application No. PCT/JP00/05220, filed on Aug. 3, 2000.

(30) Foreign Application Priority Data

Aug. 5, 1999 (JP) ................................ 11-222101

(51) Int. Cl.

| | |
|---|---|
| ***A61K 14/00*** | (2006.01) |
| ***A61K 38/00*** | (2006.01) |
| ***A61K 39/00*** | (2006.01) |
| *C07K 14/00* | (2006.01) |

(52) U.S. Cl. ....................... 424/185.1; 514/15; 530/328

(58) Field of Classification Search ....................... None
See application file for complete search history.

(56) References Cited

U.S. PATENT DOCUMENTS

| | | | | |
|---|---|---|---|---|
| 5,432,076 A * | 7/1995 | Rudd et al. | .............. | 435/372.2 |
| 5,734,023 A * | 3/1998 | Nag et al. | .................... | 530/403 |
| 6,635,623 B1 * | 10/2003 | Hoogeveen et al. | ........... | 514/44 |
| 2004/0141992 A1 | 7/2004 | Itoh et al. | | |
| 2005/0019341 A1 | 1/2005 | Itoh et al. | | |

FOREIGN PATENT DOCUMENTS

| | | | |
|---|---|---|---|
| WO | WO 97/22255 A1 * | 6/1997 | |
| WO | WO 98/46996 A2 | 10/1998 | |

OTHER PUBLICATIONS

Marchand et al (Int. J. Cancer 20: 219-230, 1999).*
Marchand et al (Exp. Opin. Biol. Ther. 1(3): 497-510, 2001).*
Bodey et al (Anticancer Research 20: 2665-2676, 2000).*
Gao et al (J. Immunother. 23: 643-653, 2000).*
Merck Manual 16th Edition, 1992, Merck Research Laboratories, Rahway, N.J., p. 21.*
Encyclopedia Brittanica Online. 2004, 2 pages, search.eb.com/eb/print?eu=76559.*
Paul (Fundamental Immunology, 2nd Edition, Raven Press, NY, 1989, p. 1006).*
Bergmann et al. J. Virol. 1994 68(8): 5306-5310.*
Wang et al. Cell. Immunol. 1992 143; 284-297.*
Perkins et al. J. Immunol. 1991 146(7): 2137-2144.*
Theobald et al. J. Exp. Med. 1998, 188(6): 1017-1028.*
Gileadi et al. Eur. J. Immuno. 1999, 29: 2213-2222.*
Eisenlohr et al. J. Exp. Med. 1992, 175: 481-487.*
Shastri et al. J. Immunol. 1995, 155: 4339-4346.*
Engelhard, V.H., Curr. Opin. Immunol. 1994, 6: 13-23.*
Guo et al. Nature, 1992, 360: 364-366.*
Wiley InterScience Journal Abstract of European J. Immunol. vol. 31, Issue 2, pp. 323-332, published online: Jan. 22, 2001.*
De Bruijin et al. Eur. J. Immunol. 1991, 21: 2963-2790.*
Boon et al (Ann. Rev. Immunol. 2006, 24: 175-208).*
Voronova, A. F. et al.: "Expression Of A New Tyrosine Protein Kinase In Stimulated By Retrovirus Promoter Insertion" Nature (London), vol. 319, No. 6055, 1986, pp. 682-685.
Rosenberg, S. A. et al.: "Immunologic And Therapeutic Evaluation Of A Synthetic Peptide Vaccine For The Treatment Of Patients With Metastatic Melanoma", Nature Medicine, Nature Publishing, Co, US, vol. 4, No. 3, Mar. 1, 1998, pp. 321-327.
Lindauer, Markus et al.: "The Molecular Basis Of Cancer Immunotherapy By Cytotoxic T Lymphocytes", Journal of Molecular Medicine (Berlin), vol. 76, No. 1, Jan. 1998, pp. 32-47.
European Search Report for EP 00 94 9982, Oct. 11, 2002.
Megumi Kikuchi, et al., "*Identification of a Sart-1-Derived Peptide Capable of Inducing HLA-A24-Restricted and Tumor-Specific Cytotoxic T Lymphocytes", Int. J. Cancer*, 1999, vol. 81, pp. 459-466.
Yasuhiro Koga, et al., "*A Human T Cell-Specific cDNA Clone (YT16) Encodes A Protein With Extensive Homology To A Family of Protein-Tyrosine Kinases", Eur. J. Immunol.* 1986, vol. 16, pp. 1643-1646.
Akio Tanaka, et al., "*DNA Sequence Encoding The Amino-Terminal Region of the Human c-src Protein: Implications of Sequence Divergence Among src-Type Kinase Oncogenes", Molecular and Cellular Biology*, May 1987, pp. 1978-1983.
Nanae Harashima, et al., "*Recognition of the Lck Tyrosine Kinase as a Tumor Antigen by Cytotoxic T Lymphocytes of Cancer Patients with Distant Metastases", Eur. J. Immunol.*, 2001, vol. 31, pp. 323-332.
Nobue Imai, et al., "*Identification of Lck-Derived Peptides Capable of Inducing HLA-A2-Restricted and Tumor-Specific CTLS in Cancer Patients with Distant Metastases", Int. J. Cancer*, 2001; vol. 94, pp. 237-242.

* cited by examiner

*Primary Examiner*—G. R. Ewoldt
*Assistant Examiner*—DiBrino Marianne
(74) *Attorney, Agent, or Firm*—Kilyk & Bowersox, P.L.L.C.

(57) ABSTRACT

The present invention relates to a tumor antigen peptide capable of inducing and/or activating HLA-A24-restricted and/or HLA-A2-restricted and tumor-specific cytotoxic T lymphocytes. The present invention also relates to a method of providing a polynucleotide encoding the peptide and a complementary strand thereto, a recombinant vector containing the polynucleotide, a transformant containing the recombinant vectors. The present invention also relates to a method for producing the peptide, an antibody against the peptide, a compound interacting with these entities and a method for screening for the compound, a pharmaceutical composition utilizing these entities, and a means for the diagnosis utilizing these entities.

3 Claims, 15 Drawing Sheets

(A)

(B)

(A)

(B)

(C)

(D)

SEQUENCE LISTING

<160> NUMBER OF SEQ ID NOS: 17

<210> SEQ ID NO 1
<211> LENGTH: 9
<212> TYPE: PRT
<213> ORGANISM: Homo sapiens

<400> SEQUENCE: 1

Thr Phe Asp Tyr Leu Arg Ser Val Leu
1               5

<210> SEQ ID NO 2
<211> LENGTH: 10
<212> TYPE: PRT
<213> ORGANISM: Homo sapiens

<400> SEQUENCE: 2

Asp Tyr Leu Arg Ser Val Leu Glu Asp Phe
1               5                   10

<210> SEQ ID NO 3
<211> LENGTH: 9
<212> TYPE: PRT
<213> ORGANISM: Homo sapiens

<400> SEQUENCE: 3

His Tyr Thr Asn Ala Ser Asp Gly Leu
1               5

<210> SEQ ID NO 4
<211> LENGTH: 9
<212> TYPE: PRT
<213> ORGANISM: Homo sapiens

<400> SEQUENCE: 4

Thr Phe Glu Tyr Leu Gln Ala Phe Leu
1               5

<210> SEQ ID NO 5
<211> LENGTH: 9
<212> TYPE: PRT
<213> ORGANISM: Homo sapiens

<400> SEQUENCE: 5

Thr Phe Glu Tyr Ile Gln Ser Phe Leu
1               5

<210> SEQ ID NO 6
<211> LENGTH: 9
<212> TYPE: PRT
<213> ORGANISM: Homo sapiens

<400> SEQUENCE: 6

Thr Phe Glu Tyr Leu Gln Ser Phe Leu
1               5

<210> SEQ ID NO 7
<211> LENGTH: 9
<212> TYPE: PRT
<213> ORGANISM: Homo sapiens

<400> SEQUENCE: 7

Thr Phe Asp Tyr Leu Gln Ser Val Leu

-continued

```
  1               5


<210> SEQ ID NO 8
<211> LENGTH: 9
<212> TYPE: PRT
<213> ORGANISM: Homo sapiens

<400> SEQUENCE: 8

Thr Phe Glu Tyr Ile Gln Ser Val Leu
  1               5


<210> SEQ ID NO 9
<211> LENGTH: 9
<212> TYPE: PRT
<213> ORGANISM: Homo sapiens

<400> SEQUENCE: 9

Thr Phe Glu Phe Leu Gln Ser Val Leu
  1               5


<210> SEQ ID NO 10
<211> LENGTH: 13
<212> TYPE: PRT
<213> ORGANISM: Artificial Sequence
<220> FEATURE:
<223> OTHER INFORMATION: Description of Artificial Sequence:Designed
      peptide base on amino acid sequence of Src family
      tyrosine kinases, which peptide has an ability to
      generate HLA-A24 restricted cytotoxic T
      lymphocytes
<221> NAME/KEY: UNSURE
<222> LOCATION: (3)
<223> OTHER INFORMATION: Xaa can be Asp or Glu.
<221> NAME/KEY: UNSURE
<222> LOCATION: (4)
<223> OTHER INFORMATION: Xaa can be Tyr or Phe.
<221> NAME/KEY: UNSURE
<222> LOCATION: (5)
<223> OTHER INFORMATION: Xaa can be Leu or Ile.
<221> NAME/KEY: UNSURE
<222> LOCATION: (6)
<223> OTHER INFORMATION: Xaa can be Arg or Gln.
<221> NAME/KEY: UNSURE
<222> LOCATION: (7)
<223> OTHER INFORMATION: Xaa can be Ser or Ala.
<221> NAME/KEY: UNSURE
<222> LOCATION: (8)
<223> OTHER INFORMATION: Xaa can be Val or Phe.
<221> NAME/KEY: UNSURE
<222> LOCATION: (10)
<223> OTHER INFORMATION: Xaa can be Glu or Asp.
<221> NAME/KEY: UNSURE
<222> LOCATION: (12)
<223> OTHER INFORMATION: Xaa can be Phe or Tyr.
<221> NAME/KEY: UNSURE
<222> LOCATION: (13)
<223> OTHER INFORMATION: Xaa can be Phe or Tyr.

<400> SEQUENCE: 10

Thr Phe Xaa Xaa Xaa Xaa Xaa Xaa Leu Xaa Asp Xaa Xaa
  1               5                  10


<210> SEQ ID NO 11
<211> LENGTH: 9
<212> TYPE: PRT
<213> ORGANISM: Homo sapiens

<400> SEQUENCE: 11

Leu Gln Asp Asn Leu Val Ile Ala Leu
  1               5
```

-continued

```
<210> SEQ ID NO 12
<211> LENGTH: 9
<212> TYPE: PRT
<213> ORGANISM: Homo sapiens

<400> SEQUENCE: 12

Lys Leu Val Glu Arg Leu Gly Ala Ala
  1               5


<210> SEQ ID NO 13
<211> LENGTH: 10
<212> TYPE: PRT
<213> ORGANISM: Homo sapiens

<400> SEQUENCE: 13

Gln Leu Gln His Gln Arg Leu Val Arg Leu
  1               5                  10


<210> SEQ ID NO 14
<211> LENGTH: 9
<212> TYPE: PRT
<213> ORGANISM: Homo sapiens

<400> SEQUENCE: 14

Lys Leu Leu Asp Met Ala Ala Gln Ile
  1               5


<210> SEQ ID NO 15
<211> LENGTH: 9
<212> TYPE: PRT
<213> ORGANISM: Homo sapiens

<400> SEQUENCE: 15

Gln Ile Ala Glu Gly Met Ala Phe Ile
  1               5


<210> SEQ ID NO 16
<211> LENGTH: 9
<212> TYPE: PRT
<213> ORGANISM: Homo sapiens

<400> SEQUENCE: 16

Asp Val Trp Ser Phe Gly Ile Leu Leu
  1               5


<210> SEQ ID NO 17
<211> LENGTH: 9
<212> TYPE: PRT
<213> ORGANISM: Homo sapiens

<400> SEQUENCE: 17

Ser Val Leu Glu Asp Phe Phe Thr Ala
  1               5
```

TUMOR ANTIGEN

This application is a continuation-in-part of International Application No. PCT/JP00/05220, having an International Filing Date of Aug. 3, 2000, which is incorporated in its entirety by reference herein.

TECHNICAL FIELD

The present invention relates generally to a novel tumor antigen, and more particularly to a peptide that is recognized by tumor-specific cytotoxic T lymphocytes, a polynucleotide encoding the peptide or a complementary strand thereto, a recombinant vector containing the polynucleotide, a transformant containing the recombinant vector, a method for producing the peptide, an antibody against the peptide, a compound having any interaction with these, and a method for screening the compound, a pharmaceutical composition utilizing these, and a means of analysis for the diagnosis utilizing these.

BACKGROUND ART

The immune system, particularly cytotoxic T lymphocytes (which, hereinafter, may be abbreviated to CTLs) play an important role in the exclusion of cancer in vivo. An infiltration of cytotoxic T lymphocytes that exhibit a toxic activity against a tumor cell has been detected at the tumor site of a cancer patient (Arch. Surg., 126: 200-205, 1990). A tumor antigen that is a target molecule for the tumor-specific cytotoxic T lymphocytes was first discovered in melanoma type cancers. A tumor antigen generated in a tumor cell is decomposed in the cell into a peptide (tumor antigen peptide) consisting of eight to eleven amino acids, which binds to a human leukocyte antigen (HLA) molecule that is the major histocompatibility complex to be displayed on the surface of the tumor cell.

HLA is a cell membrane antigen, and is expressed on almost all of eukaryotic cells. HLA is mainly classified as a class I antigen or class II antigen. The HLA recognized together with an antigen peptide by a cytotoxic T lymphocytes is a class I antigen. HLA class I antigens are further classified into HLA-A, B, C, and so on. It was reported that HLA has the genetic polymorphism. The HLA-A24 allele is found in approximately 60% of the Japanese population (in a majority, equal to 95%, the genotype is A2402), 20% of Caucasians, and 12% of Africans. The HLA-A2 allele is found in approximately 40% of Japanese, 53% of Chinese, 49% of North Caucasians, 38% of South Caucasians, and 23% of Black Africans.

A tumor antigen peptide capable of binding to the HLA has a motif in its sequence for each type of HLA. Cytotoxic T lymphocytes injure a tumor cell by recognizing a complex consisting of the tumor antigen peptide and HLA. As used herein, a tumor antigen means a protein or peptide contained in a tumor cell capable of inducing a tumor-specific cytotoxic T lymphocyte. A tumor antigen peptide means a peptide that is generated as a result of degradation of the tumor antigen in a tumor cell and can induce or activate tumor-specific cytotoxic T lymphocytes by being expressed on the surface of the cells by binding an HLA molecule. In addition, a site of the amino acid sequence capable of inducing tumor-specific cytotoxic T lymphocytes existing in a tumor antigen is called a tumor antigen epitope (tumor antigen determinant).

Recently, many genes encoding tumor antigens that can be recognized by cytotoxic T lymphocytes have been identified from cDNA of human tumor cells (Science, 254: 1643-1647, 1991; J. Exp. Med., 183: 1185-1192, 1996). Some of these genes are involved in cell proliferation and malignant transformation, including HER/neu (Proc. Natl. Acad. Sci. USA, 92: 432-436, 1995), mutant cdk (Science, 269, 1281-1284, 1995), and mutant CASP-8 (J. Exp. Med., 186: 785-793, 1997). Several other gene products such as MAGE (melanoma antigen) family (Cancer Res., 55: 3478-3482, 1995) and SART1 (J. Exp. Med. 187: 277-288, 1998) are preferentially expressed in both of malignant cells and the testis, but not in other normal cells.

Many melanoma-specific tumor antigens exist also in a normal melanocyte, including MART-1/melanA, gp100, and tyrosinase (Oncogene Res., 1: 357-374, 1987). Therefore, human tumor antigens are for the most part not truly tumor-specific antigens, but rather self-antigens that are expressed in some normal cells or tissues.

Now, in Europe and in the United States, a cancer vaccine therapy has been developed that activates cytotoxic T lymphocytes in a cancer patient by an administration of a tumor antigen peptide, and the results of clinical tests have been reported with respect to the melanoma-specific tumor antigen. For example, tumor regression has been observed in 42% of melanoma patients who received the subcutaneous injection of melanoma antigen gp100 peptide and intravenous injection of interleukin-2 (IL-2) (Nature Medicine, 4: 321, 1998). Thus, by utilizing a tumor antigen as a vaccine, an effective treatment against cancer can be achieved.

However, almost all of the identified tumor antigens are derived from melanoma, and only a few papers have been published on tumor antigens derived from epithelial cancer and adenocarcinoma, which occur at high incidence rates.

Five-year survival rate due to three known major treatment methods for cancer (operation therapy, chemotherapy, and irradiation treatment) was 41% in 1998 with respect to all kinds of cancer. However, it is so far difficult to increase the survival rate, so that the development of a new treatment method is desired other than the above-mentioned three major treatment methods.

The lck gene encoding $p56^{lck}$ protein, which is an src family membrane tyrosine kinase, has an essential role in T cell development and function. Abnormal expression of the lck gene in colon cancer cells and small lung carcinoma cells (Oncogene Res., 1: 357-374, 1987) and aberrant expression in metastatic colon cancer were reported. However, detailed roles of Lck protein in these cancer cells are still unknown, although it is suggested that Lck protein plays an important role in the process of neoplastic transformation (Cancer Res., 58: 4660-4666, 1998),

DISCLOSURE OF THE INVENTION

Considering the above-mentioned state, the present invention aims to find out and provide a new tumor antigen that is recognized by cytotoxic T lymphocytes and is useful for the specific immunotherapy for patients having adenocarcinoma and/or epithelial cancers, such as colon cancer and lung cancer.

Concretely, the purpose of the present invention is to find out and provide a peptide having an antigen epitope that is recognized by at least HLA-A2402-restricted or HLA-A2-restricted cytotoxic T lymphocytes and is encoded by the lck gene. In more detail, the purpose of the present invention is to provide a peptide that is recognized by HLA-A2402-restricted or HLA-A2-restricted cytotoxic T lymphocytes, a polynucleotide encoding the peptide or a complementary strand thereto, a recombinant vector containing the polynucleotide, a transformant containing the recombinant vector, a method for producing the peptide, an antibody against the peptide, a compound that interacts with these entities and a method for screening for such a compound, a pharmaceutical composition utilizing these entities, and a means for the diagnosis utilizing these entities.

To solve the subject, the inventor established KE4-CTL, which is an HLA-A2402-restricted and tumor-specific cytotoxic T lymphocyte, that are activated by recognizing HLA-A24 and a tumor antigen peptide, and OK-CTL and GK-CTL, which are HLA-A2-restricted and tumor-specific cytotoxic T lymphocytes, that are activated by recognizing HLA-A2 and a tumor antigen peptide, and then identified a tumor antigen capable of activating the tumor-specific cytotoxic T lymphocytes from a cDNA library of KE tumor cell line using the gene expression cloning method, and finally found out a peptide having an epitope of the tumor antigen that is recognized by HLA-A2402-restricted and/or HLA-A2-restricted cytotoxic T lymphocytes, and accomplished the present invention.

The present invention comprises:

(1) a peptide having an amino acid sequence of SEQ ID NO:1, 2, 3, 4, 5, 6, 7, 8, 9, 11, 12, 13, 14, 15, 16, or 17 of the sequence listing, (2) a peptide having the amino acid sequence shown by the formula (SEQ ID NO:10 in the sequence listing)

Thr-Phe-Xaa-Xbb-Xcc-Xdd-Xee-Xff-Leu-Xgg-Asp-Xhh-Xii, wherein Xaa is Asp or Glu, Xbb is Tyr or Phe, Xcc is Leu or Ile, Xdd is Arg or Gln, Xee is Ser or Ala, Xff is Val or Phe, Xgg is Glu or Asp, Xhh is Phe or Tyr, and Xii is Phe or Tyr, (3) an inducer of cytotoxic T lymphocytes comprising at least peptide (1) or (2), (4) a method for inducing cytotoxic T lymphocytes using peptide (1) or (2), (5) a cancer vaccine comprising at least peptide (1) or (2), (6) a polynucleotide encoding peptide (1) or (2) or a complementary strand thereto, (7) a polynucleotide that hybridizes to polynucleotide (6) or a complementary strand thereto under a stringent condition, (8) a recombinant vector comprising polynucleotide (6) or (7) or a complementary strand thereto, (9) a transformant transformed with recombinant vector (8),

(10) a method for producing a peptide, which comprises a step of culturing transformant (9),

(11) an antibody that immunologically recognizes peptide (1) or (2),

(12) a method for screening for a compound that interacts with peptide (1) or (2) and enhances the recognition ability by at least HLA-A2402-restricted and/or HLA-2-restricted cytotoxic T lymphocytes, and/or a compound that interacts with polynucleotide (6) or (7) and enhances the expression thereof, wherein at least one entity is used that is selected from a group consisting of peptides (1) and(2), polynucleotides (6) and(7), recombinant vector (8), transformant (9), and antibody (11),

(13) a compound obtained by screening method (12),

(14) a pharmaceutical composition comprising at least one entity selected from the group consisting of peptides (1) and (2), polynucleotides (6) and (7), recombinant vector (8), transformant (9), antibody (11), and compound (13) in an amount effective for treating cancer,

(15) a method for treating cancer characterized by using inducer (3) of cytotoxic T lymphocytes, cancer vaccine (5), or pharmaceutical composition (14),

(16) a method for diagnosing a disease relevant to the expression or activity of peptide (1) or (2), wherein the method comprises a step where a polynucleotide encoding (a) the polypeptide and/or (b) the peptide in a specimen derived from an individual are/is analyzed as marker(s), and

(17) a reagent kit used for method (16), wherein the kit consists of at least one entity selected from the group consisting of peptides (1) and (2), polynucleotides (6) and (7), and antibody (11).

BEST MODE FOR CARRYING OUT THE INVENTION (Identification of Lck Gene)

The inventor has been taking a notice of HLA-A24, which is a type of HLA-A molecule found in many Japanese, and established HLA-A2402-restricted tumor-specific cytotoxic T lymphocytes (KE4-CTL) that are activated by recognizing the HLA-A24 and a tumor antigen peptide from an esophageal cancer patient (Int. J. Cancer, 81: 459-466, 1999). Using the cytotoxic T lymphocytes as an effector, a tumor antigen capable of activating the cells was identified from a cDNA library of KE tumor cell line by the gene expression cloning method. The activation of the cytotoxic T lymphocytes was investigated by measuring interferon-γ (IFN-γ) produced from the cytotoxic T lymphocytes using an enzyme-linked immunosorbent assay (ELISA) kit.

As a result, it was found that one cDNA clone is recognized by HLA-A24-restricted KE4-CTLs, and activates the KE4-CTLs (see FIG. 1), and that the nucleotide sequence of the cDNA clone is 1,750-base-pair (bp)-long and has a homology to position 283-2,032 at 100% in the nucleotide sequence of lck gene. The nucleotide sequence of lck gene in this position corresponds to the amino acid sequence of position 31-506, which is almost all of the part of Lck protein consisting of 509 amino acids.

Namely, a cell, which was made to express lck gene and HLA-A2402 by the genetic engineering technique, activated KE-CTLs, so that it was confirmed that the protein encoded by lck gene is a tumor antigen capable of activating HLA-A2402-restricted CTLs.

Figure 2:
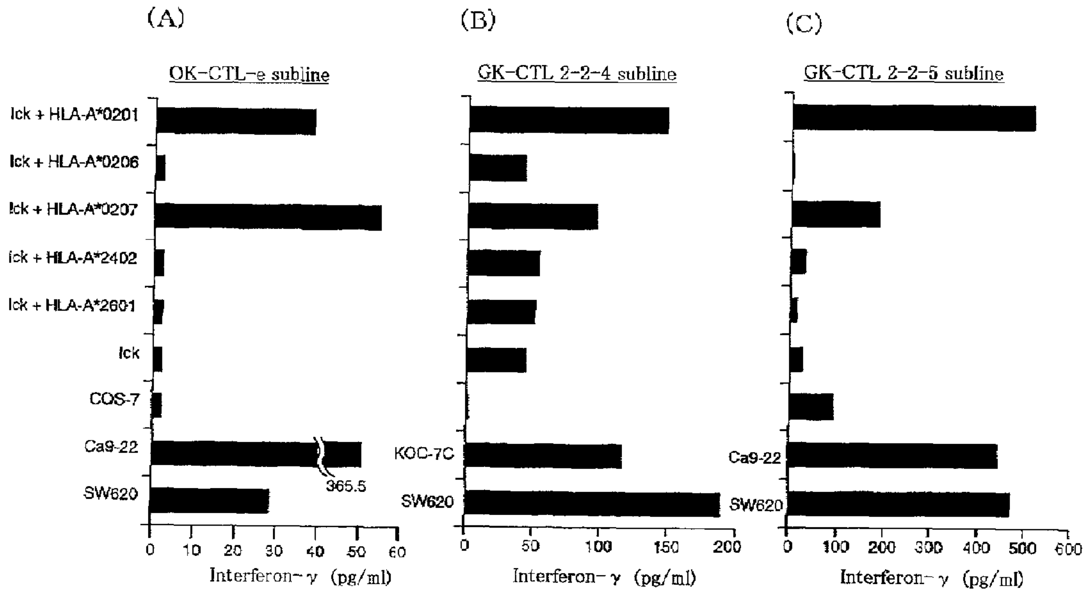
FIG. 2 illustrates the interferon-γ (IFN-γ) production by the activated HLA-A2-restricted cytotoxic T lymphocytes by the recognition of lck gene product. (A) OK-CTL-e subline was used as the HLA-A2-restricted CTLs. (B) GK-CTL2-2-4 subline was used as the HLA-A2-restricted CTLs. (C) GK-CTL2-2-5 subline was used as the HLA-A2-restricted CTLs.

In addition, Lck protein proved to be a tumor antigen capable of activating not only HLA-A24-restricted CTLs but also HLA-A2-restricted CTLs by the investigation using three HLA-A2-restricted CTLs, i.e., CTL lines established from a colon cancer patient [OK-CTL-e subline (HLA-A0207)] (J. Immunol., 163: 4999-5004, 1999) and CTL lines established from a lung cancer patient [GK-CTL2-2-4 subline and GK-CTL2-2-5 (HLA-A0206)] in a manner similar to one described above (see FIG. 2).

Thus, the lck gene proved to encode a tumor antigen epitope recognized by HLA-A24-restricted or HLA-A2-restricted and tumor-specific cytotoxic T lymphocytes.

(Tissue Distribution of Lck Protein)

Expression of Lcks (56 kD and 59 kD) at the protein level in various cells and tissues was examined by the Western blot analysis using an anti-Lck monoclonal antibody.

Lck protein was detected in all the tested malignant tumor cell lines such as squamous cell carcinoma (SCC) or adenocarcinoma cell line, and in almost all of fresh tumor tissues obtained from various organs such as esophageal carcinoma, pulmonary SCC, and pulmonary adenocarcinoma. Lck protein was expressed especially in the tissues of colon cancer, pulmonary cancer, and esophageal carcinoma at a high level, while it was not detected in any non-tumorous colon tissues at all. In addition, Lck protein was not detected in unstimulated peripheral blood mononuclear cells (PBMCs) but was detected in a cytoplasmic fraction of activated PBMCs (PHA-blast) after the stimulation by phytohemagglutinin (PHA) at 10 μg/ml for 48 h.

(Peptide Capable of Activating HLA-A2402-restricted CTL)

In order to obtain a peptide capable of binding to HLA-A2402 molecule derived from Lck protein, a peptide having an HLA-A24 binding motif was searched for in the literature, and then thirteen peptides (9-mers and 10-mers) were synthesize based on the sequence consisting of 509 amino acids of the lck gene product (Nature, 319: 682-685, 1986). Some amino acids in some of these thirteen peptides were substituted for the lck gene product.

A tumor antigen peptide capable of activating cytotoxic T lymphocytes was selected from 13 peptides by assaying IFN-γ produced from CTLs as an indicator for its CTL-activating action.

Figure 3:
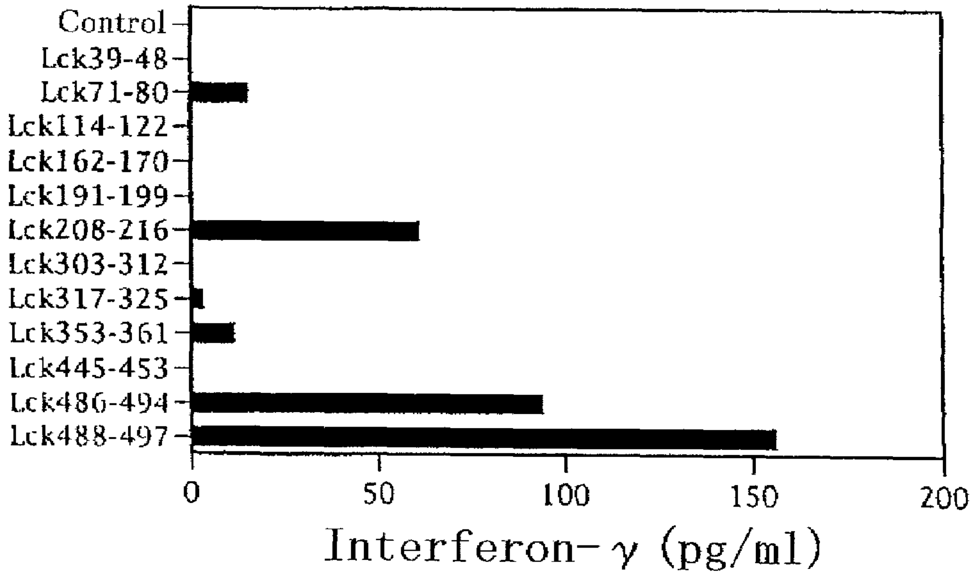
FIG. 3 illustrates an amount of the interferon-γ (IFN-γ) produced from KE-CTLs stimulated by ClR/A2402 cells pulsed with a peptide derived from Lck.

Among these peptides, three peptides [Lck208-216 (SEQ ID NO:3), Lck486-494 (SEQ ID NO:1), Lck488-497 (SEQ ID NO:2)] exhibited a CTL-activating ability, and enhanced the production of IFN-γ by CTLs (see FIG. 3). The CTL-activating ability of Lck486-494 (SEQ ID NO:1) or Lck488-497 (SEQ ID NO:2) showed a dose-dependency, which was detected at 1 nM or so. On the other hand, the activity of Lck208-216 (SEQ ID NO:3) was detected at 100 nM or higher (see FIG. 4).

The activation of KE4-CTLs by these three peptides was inhibited by anti-CD3, anti-CD8, and anti-MHC class I monoclonal antibody, but not inhibited by anti-CD4, anti-MHC class II and anti-CD13 monoclonal antibody. Therefore, KE4-CTLs proved to have a phenotype of $CD3^+$, $CD8^+$, and $CD4^-$.

(Induction of HLA-A24-restricted Cytotoxic T Lymphocyte by Peptide)

Three peptides that activate HLA-A24-restricted KE-CTLs in a dose-dependent manner [Lck208-216 (SEQ ID NO:3), Lck486-494 (SEQ ID NO:1), or Lck488-497 (SEQ ID NO:2)] also induced HLA-A24-restricted CTLs against tumor cell lines (KE4, SW620 and COLO201) expressing Lck from peripheral blood mononuclear cells (PBMCs) obtained from a colon cancer patient.

Namely, when stimulation was carried out in vitro three times using Lck208-216 (SEQ ID NO:3), Lck486-494 (SEQ ID NO:1), or Lck488-497 (SEQ ID NO:2), and further using irradiated autologous PBMCs pulsed with a corresponding peptide as antigen-presenting cells (APCs), especially PBMCs stimulated by Lck486-494 (SEQ ID NO:1) or Lck488-497 (SEQ ID NO:2) produced a greater amount of IFN-γ in the reaction against HLA-A24$^+$ tumor cell (KE4 and SW620) than in the reaction against HLA-A24$^-$ tumor cell (COLO201).

On the other hand, from PBMCs obtained from a healthy donor HLA-A24-restricted CTLs were not induced by these three peptides, when stimulation was performed using irradiated autologous PBMCs pulsed with one of these three peptides as antigen-presenting cells (APCs), (see Table 3). However, when the stimulation was carried out using dendritic cells (DCs) that were pulsed with a peptide as APCs, these three peptides induced HLA-A24-restricted CTLs from PBMCs obtained from a healthy donor.

In addition, CTL activity induced by the above-mentioned peptide was confirmed by the $^{51}$Cr-release test. PBMCs stimulated with these three peptides derived from Lck lysed HLA-A24$^+$ KE tumor cells and SW620 tumor cells, but did not lyse HLA-A24$^+$ PHA-activated T lymphocytes obtained from a healthy donor or HLA-A24$^-$ COLO201 tumor cells.

The above-mentioned peptides derived from Lck could induce HLA-A24-restricted and tumor-specific cytotoxic T lymphocytes in PBMCs of a colon cancer patient. In addition, a peptide derived from Lck could not induce HLA-A24-restricted CTL activity against a tumor cell with respect to PBMCs of a healthy donor. These results suggest that T lymphocytes in the peripheral blood of a healthy donor are immunologically tolerant to Lck. The Lck peptide according to the present invention can induce CTLs in PBMCs of a colon cancer patient.

(Induction of HLA-A24-restricted CTL by Peptide Derived from Src Family)

Among the above-mentioned three peptides capable of inducing CTLs that recognize HLA-A24$^+$ tumor cell line, two peptides were found to have a homology on the amino acid sequences, that is Lck486-494 (SEQ ID NO:1) (TFDYLRSVL) and LcK488-497 (SEQ ID NO:2) (DYLRSVLEDF) (amino acid sequence is given both in one-letter symbols and three-letter symbols hereafter). CTLs that recognize the amino acid sequence DYLRSV (SEQ ID NO:46) which is a common region for two peptides as an epitope, are assumed to have relevance to tumor rejection.

Search for a peptide having a homology to the amino acid sequence revealed that some tyrosine kinases belonging to the Src family including Lck (Ann. Rev. Biochem. 54: 897-930, 1985) contain a homologous peptide (see Table 5).

Peptides that were synthesized based on the amino acid sequence of a peptide derived from the Src family, i.e., Src511-519 (SEQ ID NO:4) (TFEYLQAFL), Yes508-516 (SEQ ID NO:5) (TFEYIQSFL), Fyn512-520 (SEQ ID NO:6) (TFEYLQSFL), Lyn489-497 (SEQ ID NO:7) (TFDYLQSVL), Hck503-511 (SEQ ID NO:8) (TFEYIQSVL), and Blk482-490 (SEQ ID NO:9) (TFEFLQSVL) also exhibited an ability to activate HLA-A24-restricted CTL that is comparable to a peptide derived from Lck or more.

Peptides according to the present invention also include a peptide that has the amino acid sequence shown by the following formula derived by the amino acid sequence of the above-mentioned homologous peptide, and is recognized at least by HLA-A2402-restricted cytotoxic T lymphocytes: Thr-Phe-Xaa-Xbb-Xcc-Xdd-Xee-Xff-Leu-Xgg-Asp-Xhh-Xii (SEQ ID NO:10), wherein Xaa is Asp or Glu, Xbb is Tyr or Phe, Xcc is Leu or Ile, Xdd is Arg or Gln, Xee is Ser or Ala, Xff is Val or Phe, Xgg is Glu or Asp, Xhh is Phe or Tyr, and Xii is Phe or Tyr.

(Induction of HLA-A24-restricted Cytotoxic T Lymphocyte in Cancer Patient by Peptide Derived from Src Family)

The above-mentioned peptide derived from the Src family could induce HLA-A24-restricted cytotoxic T lymphocytes from PBMCs obtained from a cancer patient. Namely, PBMCs obtained from a cancer patient that were stimulated with a peptide derived from the Src family reacted with a KE4 cell and a SW620 cell to produce IFN-γ. Production of IFN-γ from PBMCs was induced by Lck486-494 (SEQ ID NO:1, 4 cases among 7 cases of cancer patient), Src511-519 (SEQ ID NO:4, 2 cases among 3 cases), Yes508-516 (SEQ ID NO:5, 1 case among 3 cases), Fyn512-520 (SEQ ID NO:6, 1 case among 2 cases), Hck503-511 (SEQ ID NO:8, 2 cases among 2 cases), and Blk482-490 (SEQ ID NO:9, 1 case among 2 cases).

Three Lck peptides and peptides derived from Src family according to the present invention can induce HLA-A24-restricted and tumor-specific cytotoxic T lymphocytes in PBMCs of a colon cancer patient. Therefore, peptides according to the present invention can be used as an agent to induce tumor-specific cytotoxic T lymphocytes and as a method for inducing tumor-specific cytotoxic T lymphocytes. In addition, Lck is detected in a majority of cancer tissues including colon, lung and esophagus. The HLA-A24 allele is detected in approximately 60% of the Japanese population (in a majority, equal to 95%, the genotype is A2402), 20% of Caucasians, and 12% of Africans (HLA 1991, Vol.1: 1065-1220, Oxford: Oxford Scientific Publications, 1992). Therefore, peptides according to the present invention can be used in the specific immunotherapy for a relatively large number of cancer patients.

(Peptide Capable of Activating HLA-A2-restricted Cytotoxic T Lymphocyte)

Since Lck protein is recognized also by HLA-A2-restricted CTLs, a peptide having an HLA-A2 binding motif was searched for in the literature in order to obtain peptides derived from Lck capable of binding to HLA-A2 molecule, and 24 kinds of peptides (9-mers and 10-mers) were synthesized based on the sequence consisting of 509 amino acids of lck gene product (Nature, 319: 682-685, 1986). The capability of each peptide for CTL activation was investigated by assaying IFN-γ produced from CTLs as an indicator, wherein the OK-CTL line or GK-CTL subline 2-2-4 was used as a CTL.

Figure 13:
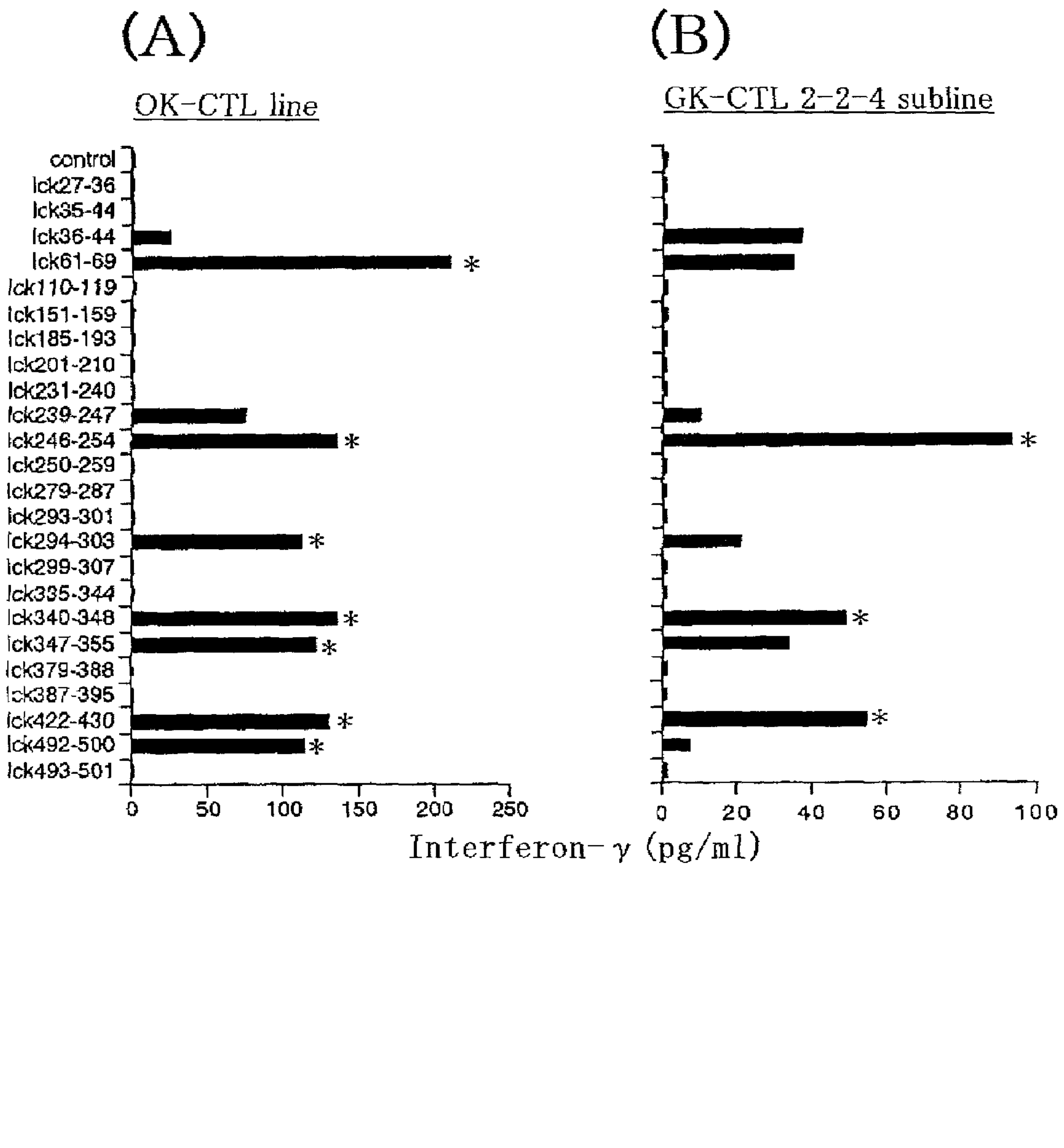
FIG. 13 illustrates the result of the analysis of HLA-A2-restricted CTL-activating ability of a peptide derived from Lck. (A) OK-CTL line was used as the HLA-A2-restricted CTL. (B) GK-CTL2-2-4 subline was used as the HLA-A2-restricted CTL.
Figure 14:
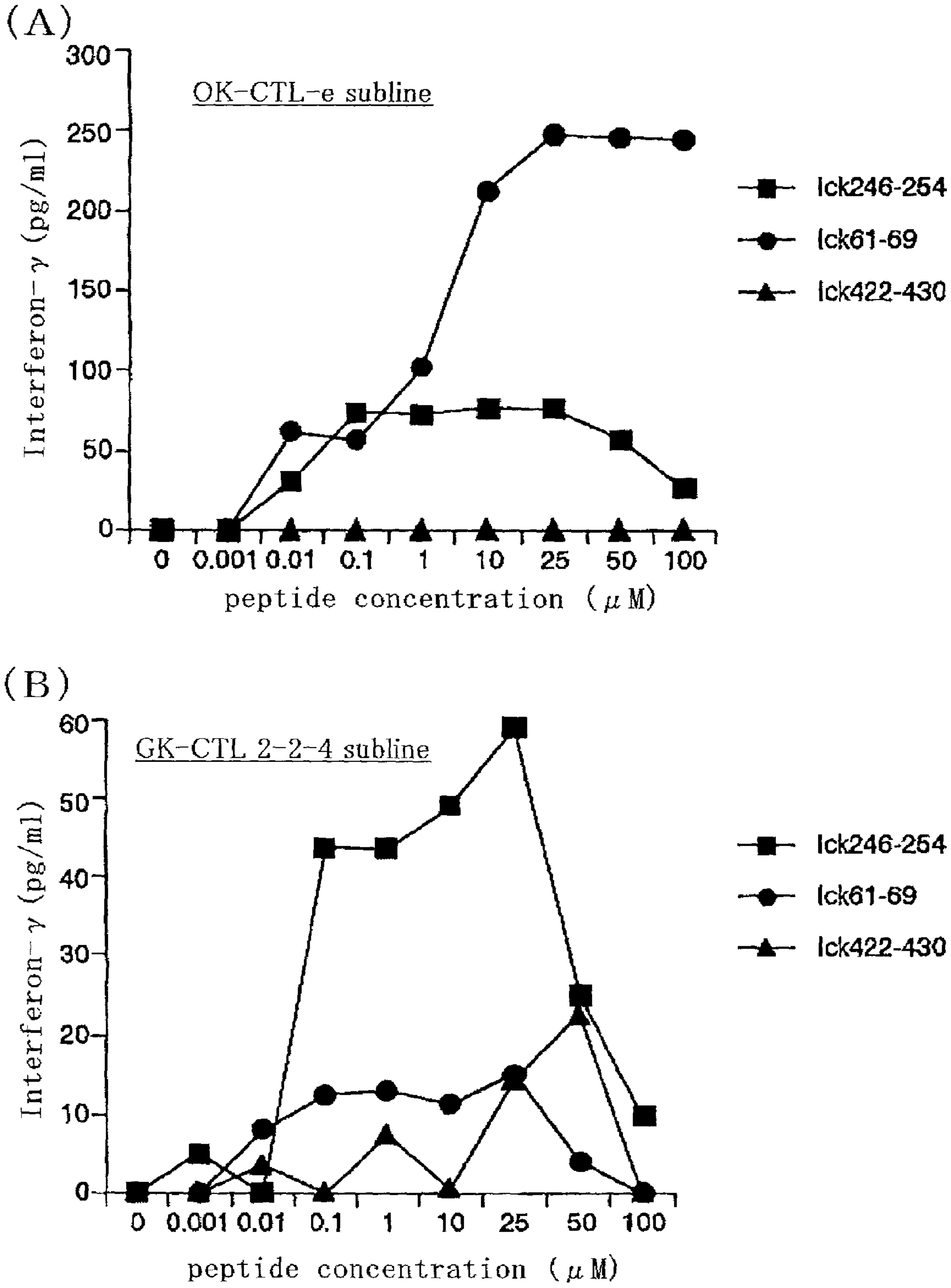
FIG. 14 illustrates the dose-dependent activation of HLA-A2-restricted CTLs of a peptide derived from Lck. (A) OK-CTL-e subline was used as CTLs. (B) GK-CTL2-2-4 subline was used as CTLs. (C) GK-CTL2-2-5 subline was used as CTLs.
Figure 14:
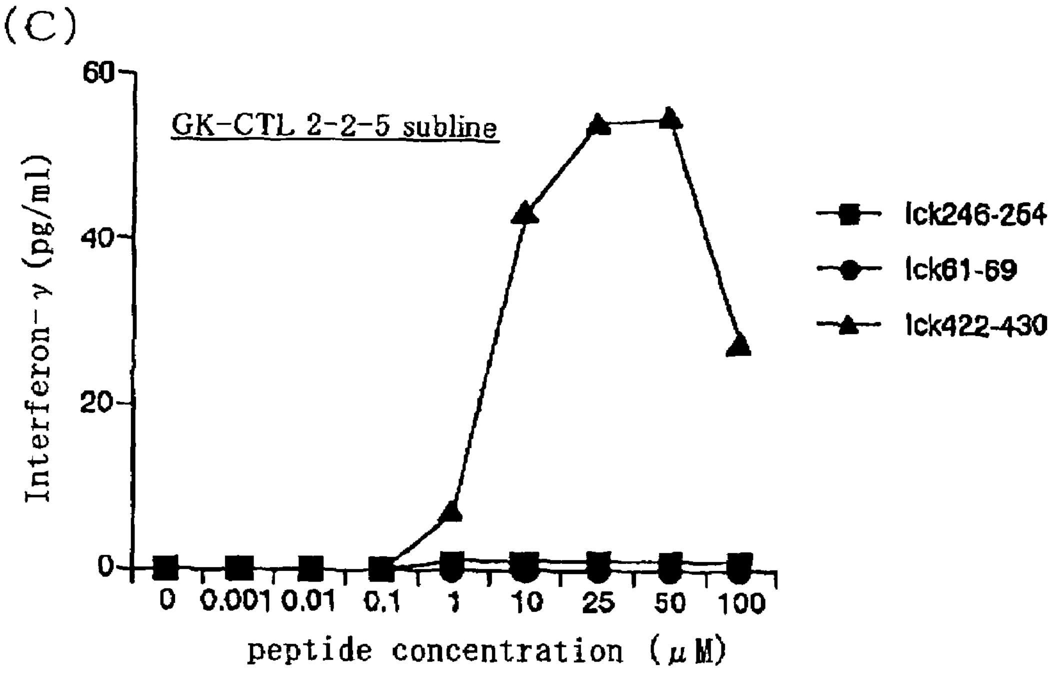

Among these peptides, 7 peptides [Lck61-69 (SEQ ID NO:11), Lck246-254 (SEQ ID NO:12), Lck294-303 (SEQ ID NO:13), Lck340-348 (SEQ ID NO:14), Lck347-355 (SEQ ID NO:15), Lck422-430 (SEQ ID NO:16), or Lck492-500 (SEQ ID NO:17)] could activate CTLs, and enhanced the IFN-γ production by CTLs [see FIGS. 13(A) and (B)]. There seemed to be a dose-dependency on the ability of Lck61-69 (SEQ ID NO:11), Lck246-254 (SEQ ID NO:12), or Lck422-430 (SEQ ID NO:16) to activate CTLs [see FIGS. 14(A), (B) and (C)].

(Induction of HLA-A2-restricted Cytotoxic T Lymphocyte by Peptide)

In addition, among three peptides that activate HLA-A2-restricted CTLs with a dose-dependency [Lck61-69 (SEQ ID NO:11), Lck246-254 (SEQ ID NO:12), and Lck422-430 (SEQ ID NO:16)], Lck246-254 (SEQ ID NO:12) or Lck422-430 (SEQ ID NO:16) induced HLA-A2-restricted CTLs against tumor cell lines Panc-1 and SW620 from PBMCs of a metastatic colon cancer patient.

Figure 15:
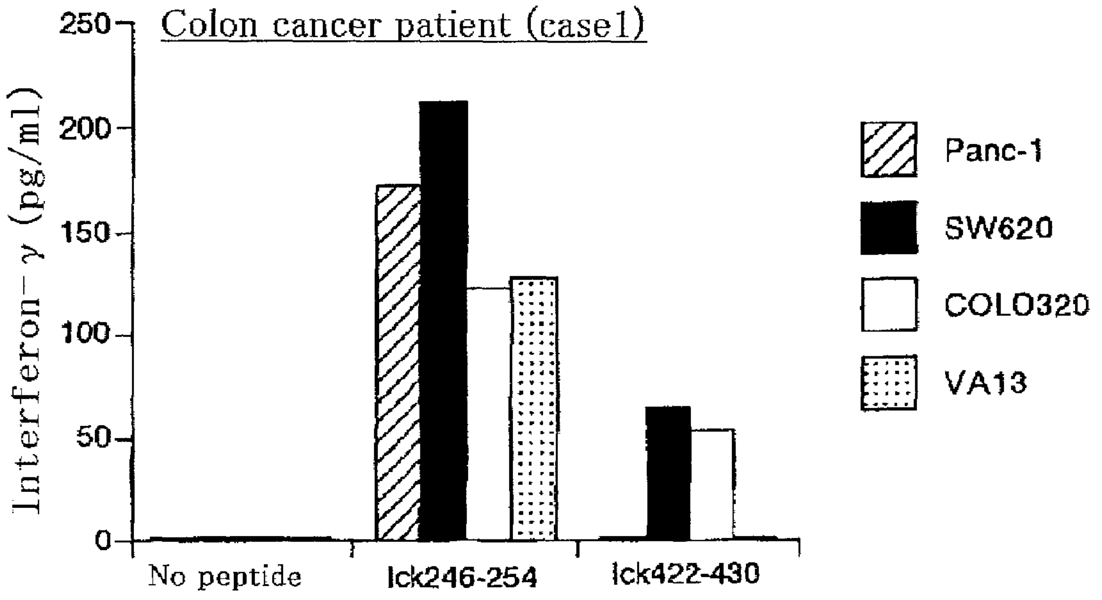
FIG. 15 indicates that a peptide derived from Lck can induce HLA-A2-restricted cytotoxic T lymphocytes from peripheral blood mononuclear cells (PBMCs) of a cancer patient. (A) The induction of CTLs from PBMCs derived from colon cancer patient (case 1) was investigated using the IFN-γ production as an indicator. (B) The induction of CTLs from colon cancer patient (case 1) was confirmed by the cytotoxicity test. (C) The induction of CTLs from PBMCs derived from colon cancer patient (case 2) was investigated using the IFN-γ production as an indicator. (D) The induction of CTLs from colon cancer patient (case 2) was confirmed by the cytotoxicity test.
Figure 15:
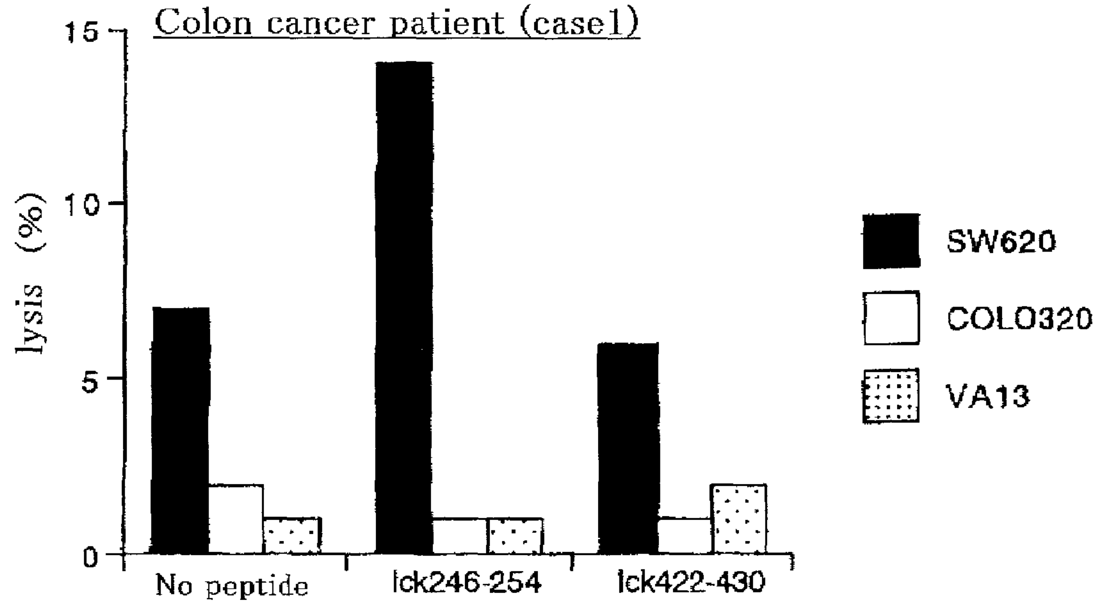
Figure 15:
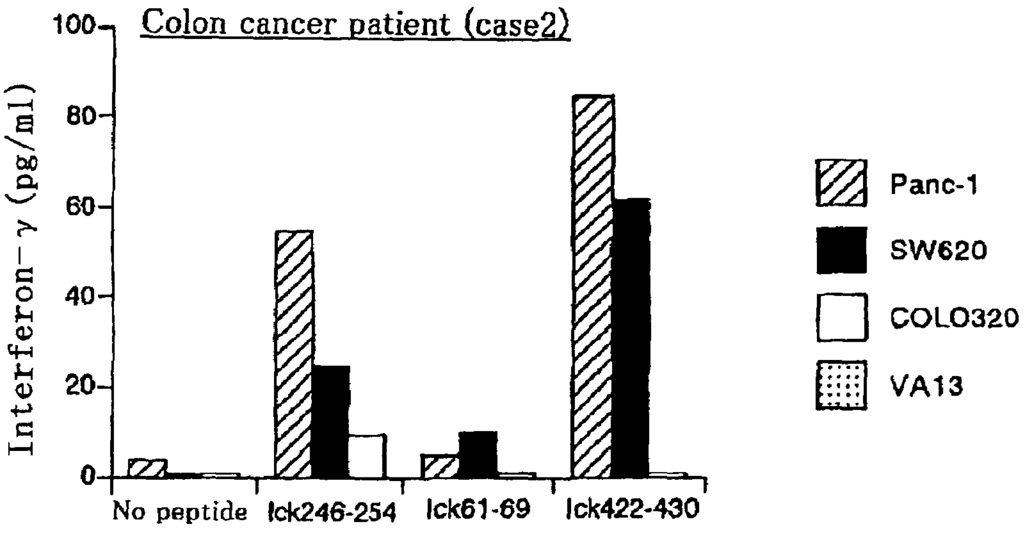
Figure 15:
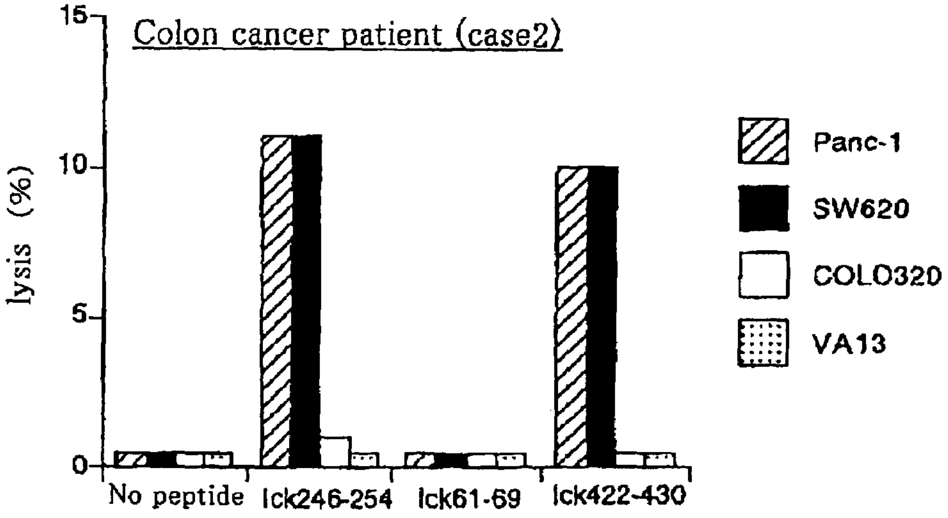

Namely, when PBMCs of a metastatic colon cancer patient were stimulated in vitro three times with one of these three peptides and then, using irradiated autologous PBMCs pulsed with a corresponding peptide as antigen-presenting cells (APCs), PBMCs of the colon cancer patient that were stimulated with Lck246-254 (SEQ ID NO:12) or Lck422-430 (SEQ ID NO:16) did not react with HLA-A2$^-$ colon cancer cell line COLO320, but did react with HLA-A2$^+$ colon cancer cell line SW620 and HLA-A2$^+$ pancreatic cancer cell line Panc-1 to produce INF-γ [see FIGS. 15(A) and (C)] and lyse HLA-A2$^+$ tumor cells [see FIGS. 15(B) and (D)].

(Induction of HLA-A2-restricted Cytotoxic T Lymphocyte in Cancer Patient)

Lck246-254 (SEQ ID NO:12) and Lck422-430 (SEQ ID NO:16) could induce HLA-A24-restricted CTLs not only from PBMCs obtained from a colon cancer patient, but also from PBMCs obtained from a metastatic pulmonary cancer patient and an esophagus cancer patient. The induction of HLA-A2-restricted CTLs was investigated using the production of IFN-γ against HLA-A2$^+$ colon cancer cell line SW620 as an indicator. HLA-A2-restricted CTLs were induced in PBMCs by Lck246-254 (SEQ ID NO:12, 2 cases among 6 cases of cancer patient) or Lck422-430 (SEQ ID NO:16, 3 cases among 6 cases of cancer patient) (see Table 8). Therefore, these three peptides can be used as inducers for and a method for inducing cytotoxic T lymphocytes. In addition, the HLA-A2 allele is found in approximately 40% of the Japanese population, 49% of North Caucasians, 38% of South Caucasians, 23% of Africans, and 53% of Chinese (HLA 1991, Vol.1: 1065-1220, Oxford Scientific Publications, 1992). Therefore, these peptides are applicable for use in the specific immunotherapy for a relatively large number of patients.

(Peptides)

A peptide according to the present invention is a peptide having the amino acid sequence of SEQ ID NO:1, 2, 3, 4, 5, 6, 7, 8, 9, 11, 12, 13, 14, 15, 16, or 17 in the sequence listing. The peptide according to the present invention can induce or activate HLA-A24-restricted or HLA-A2-restricted cytotoxic T cells.

A peptide according to the present invention can be a peptide having the amino acid sequence of SEQ ID NO:10 in the sequence listing and can induce and/or activate at least HLA-A24-restricted cytotoxic T lymphocytes. The peptide capable of inducing or activating HLA-A24-restricted cytotoxic T lymphocytes can be selected by the method described below.

A peptide according to the present invention can be a peptide capable of inducing and/or activating both HLA-24-restricted CTLs and HLA-2-restricted CTLs.

Based on thus specified peptides, using at least the strength of the recognition property by HLA-A2402-resricted and/or HLA-A2-restricted cytotoxic T lymphocytes as an index, peptides are also provided having amino acid sequences with mutation or induced mutation such as deletion, substitution, and addition of one amino acid or more. Mutation or induced mutation such as deletion, substitution, and addition can be introduced by well-known means such as Ulmer's technique (Ulmer, L. M., Science, 219, 666, 1983). In addition, some modification can be made on these available peptides to such an extent that does not cause a remarkable change in their function, for example, modification of the constitutive amino group or carboxyl group.

With respect to the protein encoded by the lck gene, some variants are known having a different amino acid sequence in part that are presumed to be based on the polymorphism (Nature, 319: 682-685, 1986; Eur. J. Immunol., 16: 1643-1646, 1986; J. Cell. Biochem., 38, 117-126, 1988; Gene, 84: 105-113, 1989). Peptides according to the present invention include peptides that are derived from the lck gene product having a different amino acid sequence and can induce HLA-A24-restricted and/or HLA-A2-restricted CTLs.

For example, Lck488-497, which is one of the peptides according to the present invention, has the amino acid sequence DYLRSVLEDF described in SEQ ID NO:2 of the sequence listing, while the amino acid sequence of position 488-497 based on the amino acid sequence of Lck protein reported in Nature, 319: 682-685, 1986 is DYLRSVLDDF (SEQ ID NO: 18), which is also included in HLA-A24-binding motif.

Peptides according to the present invention are tumor antigenic peptides capable of inducing and/or activating HLA-A24-restricted and/or HLA-A2-restricted tumor-specific cytotoxic T lymphocytes, and can be used to induce and/or activate tumor-specific cytotoxic T lymphocytes. Namely, peptides according to the present invention can be used for the specific immunotherapy for cancer, for example, as a cancer vaccine.

(Polynucleotide)

Polynucleotides and complementary strands thereto according to the present invention are polynucleotides encoding amino acids of peptides of SEQ ID NO:1, 2, 3, 4, 5, 6, 7, 8, 9, 11, 12, 13, 14, 15, 16 or 17, or peptides having mutation or induced mutation such as deletion, substitution, and addition of one amino acid or more in the amino acid sequences of these peptides and recognized at least by HLA-A2402 restricted and/or HLA-A2 restricted cytotoxic T lymphocytes, and complementary strands thereto. In addition, polynucleotides according to the present invention include polynucleotides that hybridize to these polynucleotides under a stringent condition. In the case where the polynucleotide molecule is a DNA molecule, "a DNA molecule that hybridizes to a DNA molecule under a stringent condition" can be obtained, for example, by the method described in the above-mentioned "Molecular Cloning". "To hybridize under a stringent condition" herein means that a signal of positive hybridization is still observed even after, for example, incubating at 42° C. in a solution containing 6×SSC, 0.5% SDS and 50% formamide, followed by washing at 68° C. in a solution containing 0.1×SSC and 0.5% SDS.

Polynucleotides according to the present invention provide the genetic information useful for producing peptides according to the present invention, and can be utilized also as reagents and standards of nucleic acid.

(Transformant)

The present invention can provide peptides according to the present invention by the genetic recombination technique utilizing well-known hosts such as *Escherichia coli,* yeast, *Bacillus subtilis,* insect cell, and retrovirus. It was confirmed that peptides according to the present invention are recognized by cytotoxic T lymphocytes as a simple protein, and the glycosylation of a protein is not needed, so that a host can be easily selected considering only the productivity in the production by the genetic recombination technique.

For transformation a well-known method is applicable, for example, using plasmid, chromosome, virus, and so on as a replicon transformation of a host can be carried out. As a more preferable system, the integration-into-a chromosome method can be used considering the stability of the gene. Simply, however, the autonomous replication system using a plasmid can be used. Vectors are selected considering the kind of the host selected, and consist of a gene sequence to be expressed and a gene which has a functional portion of replication and regulation. Promoter, ribosome-binding site, terminator, signal sequence, enhancer, and the like can be used in combination, wherein the combination is selected depending on whether the host is a prokaryote or eukaryote.

Transformants can be cultured under a well-known condition suitable for each host. The peptide is produced by the subcultivation or batch culture using the amount of the transformant in the medium or the physiological activity of the peptide to be expressed/produced, particularly the recognition property by the cytotoxic T lymphocyte as an index.

(Chemical Synthesis)

The peptides according to the present invention can be produced also by the method known in the general peptide chemistry. "Peptide Synthesis, Maruzen, 1975" and "Peptide Synthesis, Interscience, New York 1996" can be exemplified, but known methods are widely available.

(Collecting Peptide)

Peptides according to the present invention can be purified/collected by the combination of the gel filtration chromatography, the ion column chromatography, the affinity chromatography, and the like using the recognition property by cytotoxic T lymphocytes as an index, or by the fractionation based on their solubility using ammonium sulfate, alcohol, and the like. A method to specifically adsorb/collect a peptide by a polyclonal antibody or monoclonal antibody, that is prepared against the peptide, is more preferably used.

(Antibody)

Antibodies that immunologically recognize peptides according to the present invention can be prepared by well-known methods of antibody preparation, for example, by administration of a peptide according to the present invention to an animal in the presence or absence of an adjuvant with or without linking to a carrier so as to induce the immune response such as humoral response and/or cellular response. Any carrier can be used as long as it is not harmful to the host, such as cellulose, polymerized amino acid, and albumin. As an immunized animal, a mouse, rat, rabbit, goat, horse, and so on, is preferably used.

Polyclonal antibodies can be obtained from the serum of an animal immunized by peptides according to the present invention by well-known methods, preferably, such as immunoaffinity chromatography.

Monoclonal antibodies are produced by collecting antibody-producing cells from the above-mentioned immunized animal, followed by introducing a well-known transformation means with cells which can proliferate infinitely.

Thus obtained polyclonal antibodies or monoclonal antibodies can be utilized as antibodies for purifying peptides according to the present invention, or as reagents, labelling markers, and so on.

(Screening)

Peptides according to the present invention, polynucleotides encoding the peptides and complementary strands thereto, cells transformed based on the information concerning these amino acid sequences and nucleotide sequences, and antibodies immunologically recognizing peptides according to the present invention, or a combination of these provide an effective means for screening for a compound capable of inducing or activating cytotoxic T lymphocytes. The screening method can be constructed utilizing a well-known screening system for medical compounds. Compounds obtained by the screening method according to the present invention are also objects of the present invention. Such compounds can be compounds enhancing the recognition properties of peptides according to the present invention by HLA-A2402-restricted and/or HLA-A2-restricted CTLs, compounds enhancing the expression by the interaction with polynucleotides according to the present invention, compounds capable of inducing or activating cytotoxic T lymphocytes in a manner similar to peptides according to the present invention, or compounds enhancing the induction or activation of CTLs by peptides according to the present invention.

(Pharmaceutical Composition)

The present invention provides pharmaceutical compositions containing one or more of the following: peptides according to the present invention, polynucleotides encoding the peptides and complementary strands thereto, vectors prepared based on these amino acid sequences and nucleotide sequences, cells transformed by the vectors, antibodies immunologically recognizing peptides according to the present invention, compounds enhancing the recognition properties by HLA-A2402-restricted and/or HLA-A2-restricted CTLs of peptides according to the present invention and/or compounds enhancing the expression by the interaction with polynucleotides according to the present invention that can be obtained by the screening method according to the present invention. Pharmaceutical compositions according to the present invention are useful for treating cancers.

For example, a pharmaceutical composition containing peptide(s) according to the present invention can be used, for example, as a cancer vaccine. In such a case, in order to activate the cell-mediated immunity, a peptide according to the present invention can be used in the presence or absence of an appropriate adjuvant with or without linking to a carrier. Any carrier can be used as long as it is not harmful to the human body, such as cellulose, polymerized amino acid, and albumin. The composition can be in an appropriate form by applying a well-known method for a peptide preparation. The dosage level depends on the recognition property by cytotoxic T lymphocytes, and is generally 0.01 mg to 100 mg/day/adult, preferably 0.1 mg to 10 mg/day/adult (as an amount of a substance having the activity). Such a dose can be administered once every several days or several months.

Alternately, an effective action of a cancer vaccine can be obtained also by collecting a mononuclear cell fraction from the peripheral blood of a patient, culturing the fraction with a peptide according to the present invention, followed by returning the mononuclear cell fraction containing CTLs induced back into the blood of the patient. Culture conditions such as the concentration of mononuclear cells and the concentration of the peptide when they are cultured can be easily determined by common experiments. In addition, substances having an ability to lead the growth of lymphocytes, such as interleukin-2, can be added to the medium.

Polynucleotides encoding the peptides according to the present invention and complementary strands thereto are useful for the gene therapy of cancer. Both a method in which these DNAs are carried in a vector and directly introduced in vivo, and a method in which cells are collected from a donor, followed by introducing DNAs being carried in a vector in vitro, can be utilized. Among vectors such as retrovirus, adenovirus, and vaccinia virus, retrovirus-related ones are recommended. Needless to say, these viruses have a defect in replication. The amount of administration of a polynucleotide encoding a peptide according to the present invention can depend on the recognition property by the cytotoxic T lymphocyte, but is generally 0.1 μg to 100 mg/day/adult, preferably 1 μg to 50 mg/day/adult. This dose can be administered once every several days to several months.

(Method and Reagent Kit for Diagnosis)

Peptides according to the present invention are useful as a method for diagnosing diseases that are related to the expression of the peptides (particularly digestive system cancer).

The diagnosis is carried out by assaying the amount of a corresponding nucleic acid sequence utilizing the interaction/reactivity to the nucleic acid sequence encoding the peptide and/or determining tissue distribution of the peptide in an individual and/or determining the presence and amount of the peptide in a specimen derived from an individual. Namely, a peptide according to the present invention is to be assayed as the diagnosis marker. The assay method can be base on well-known antigen-antibody reaction systems, enzyme reaction systems, PCR reaction systems, and so on. The present invention also includes a reagent kit used for the above-mentioned diagnosis method. The reagent kit according to the present invention can contain one or more of the followings according to the present invention: peptides, polynucleotides encoding the peptides, and/or antibodies recognizing the peptides.

EXAMPLES

The present invention may be illustrated in detail with the following examples, but is not limited thereto.

Example 1

(Identification of Lck Gene)

In order to obtain a tumor antigen capable of activating cytotoxic T lymphocytes, VA13 cells transfected with a total of $10^5$ cDNA clones prepared from a cDNA library of KE4 tumor cell together with HLA-A2402 were used as a stimulator, and were co-cultured with CTLs to give a cDNA clone that activates CTLs. The activation of CTLs was assayed using the IFN-γ production as an indicator. This method permits identifying a gene encoding a tumor-rejecting antigen (J. Exp. Med. 187: 277-288, 1998).

Specifically, the CTLs used as the effector cells were HLA-A2402-restricted tumor-specific cytotoxic T lymphocytes (KE4-CTL), which were established from an esophageal carcinoma patient (Int. J. Cancer, 81: 457-466, 1999). In addition, in order to obtain a tumor antigen, the poly(A)$^+$RNA of the KE4 tumor cells was converted to cDNA, and ligated to SalI adaptor to insert into the expression vector pSV-SPORT-1 (GIBCO BRL). cDNA of HLA-A2402 or HLA-A0201 (control) was obtained by the reverse transcription-PCR (RT-PCR), and was cloned into the eukaryote expression vector pCR3 (Invitrogen). 200 ng of plasmid DNA pool or clones of the KE4 cDNA library and 200 ng of HLA-A2402 cDNA were mixed with 1 μl of lipofectin in 70 μl of OPTI-MEM (GIBCO BRL) for 15 min.

A 30 μl of the mixture was then added to VA13 cells ($2\times10^4$) and incubated for 5 h. Next, 200 μl of RPMI-1640 medium containing 10% of FCS was added, and the mixture were cultured for 2 days followed by the addition of KE4-CTLs ($10^4$ cells/well). After an 18 h incubation, 100 μl of the supernatant was collected to measure IFN-γ by an ELISA kit as described previously (J. Exp. Med. 187: 277-288, 1998).

Figure 1:
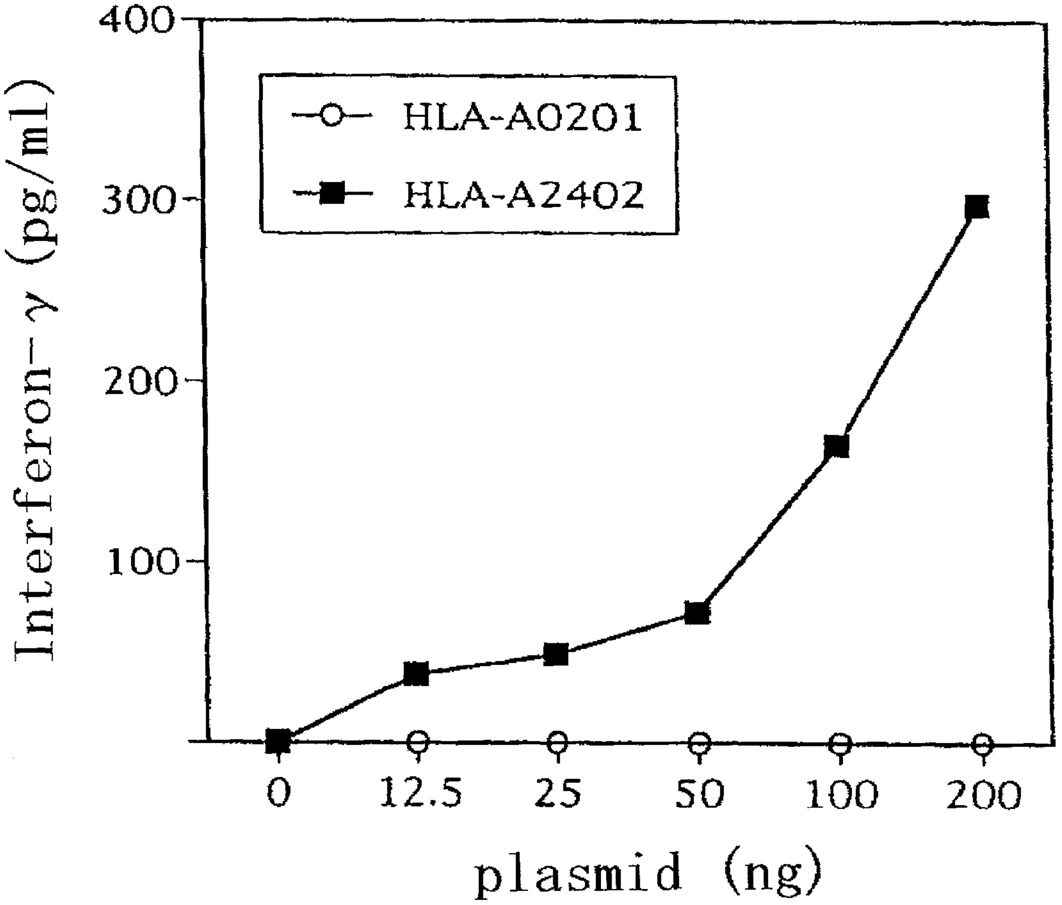
FIG. 1 illustrates the interferon-γ (IFN-γ) production by the activated HLA-A24-restricted cytotoxic T lymphocytes (KE4-CTL) by the recognition of lck gene product.

As a result, one clone (clone 21) was found to activate HLA-A24-restricted KE4-CTLs (FIG. 1). The nucleotide sequence of this cDNA clone proved to be 1,750-bp-long, and to have a homology of 100% with that of the lck gene at position 283-2,032 that is corresponding to the amino acid sequence at position 31-506 of the Lck protein consisting of 509 amino acids. Namely, it was suggested that the protein encoded by the lck gene is a tumor antigen capable of activating CTLs in an HLA-A2402-restricted manner.

In addition, the Lck protein is also proved to be a tumor antigen capable of activating not only HLA-A24-restricted CTLs, but also HLA-A2-restricted CTLs by using three HLA-A2-restricted CTLs, i.e., OK-CTL-e subline (HLA-A0207) that is a subline of CTL line (OK-CTL) established from a colon cancer patient (J. Immunol., 163: 4999-5004, 1999), and GK-CTL2-2-4 subline (HLA-A0206) and GK-CTL2-2-5 subline (HLA-A0206) that are two sublines of the CTL line (GK-CTL) established from a pulmonary cancer patient in place of HLA-A2402-restrictred KE-CTL as an effector cell, and using VA13 cells transfected with the lck gene and HLA-A0201, HLA-A0206, HLA-A0207, HLA-A2402, or HLA-A2601 as a stimulator [FIGS. 2(A), (B) and (C)].

Example 2

(Expression of Lck Protein)

The expression of Lcks (56 kD and 59 kD) at the protein level in various cells and tissues was investigated by Western blot analysis with a monoclonal anti-Lck antibody.

The examination was carried out for primary colon cancer (n=49), non-neoplastic colon (n=5), pulmonary cancer [adenocarcinoma: n=8, squamous cell carcinoma (SCC): n=8], and esophageal carcinoma cells. The colon cancer cell lines (COLO201, COLO205, COLO320, HCT116, and SW620), pulmonary cancer cell lines (LK87: adenocarcinoma cell, and LK79: small cell carcinoma), and esophageal carcinoma cell line (KE4) were also examined.

Specimens were lysed with a buffer containing 10 mM Tris-HCl, pH7.4, 150 mM NaCl, 0.5% Triton X-100, 0.2 mM PMSF (Sigma Chemical Co.), and 0.03 trypsin inhibitor unit/ml of aprotinin, sonicated, and centrifuged at 14,000 rpm for 20 min. The supernatant obtained was used as a cytosol fraction. The lysate was separated by 10% SDS-PAGE.

The proteins obtained in the acrylamide gel were blotted onto Hybond™-polyvinylidine difluoride membrane (Amersham) and were incubated with the monoclonal anti-Lck antibody (Santa Cruz) for 4 h at room temperature. The other methods of Western blot analysis were carried out according to the methods previously described (Int. J. Cancer, 54: 158-165, 1995).

Lck proteins were detected in both unstimulated peripheral blood mononuclear cells (PBMCs), and phytohemagglutinin activated PBMCs (PHA-blast). In addition, Lck proteins were detected in all 7 colon cancer cell lines tested, and several malignant tumor cell lines, including esophageal cancer, pulmonary cancer, gastric cancer, and uterine cancer, as well as in the majority of fresh tumor tissues obtained from various organs, including colon cancer, esophageal cancer, pulmonary cancer, uterine cancer, and cerebral tumor. They were also detected in some non-tumorous colon tissues, esophageal tissues, and uterine tissues (Table 1).

TABLE 1

| | Expression of Lck protein | |
|---|---|---|
| Species and source of cell | Cell line | Tissue |
| Normal cell | | |
| Peripheral blood mononuclear cell | 2/2 | — |
| PHA-blast | 2/2 | — |
| COS-7/VA13 | 0/2 | — |
| Non-tumorous part of colon tissue | — | 4/6 |
| Non-tumorous part of esophageal tissue | — | 4/6 |
| Non-tumorous part of uterine tissue | — | 4/6 |

TABLE 1-continued

| Species and source of cell | Expression of Lck protein Cell line | Tissue |
|---|---|---|
| Cancer cell | | |
| Colon cancer | 7/7 | 38/49 |
| Esophageal cancer | 6/14 | 5/9 |
| Pulmonary cancer | 4/17 | 4/10 |
| Gastric cancer | 2/8 | ND |
| Uterine cancer | 5/7 | 55/64 |
| Ovarian cancer | 0/12 | ND |
| Hepatic cell cancer | 0/13 | ND |
| Osteosarcoma | 0/16 | ND |
| Primary cerebral tumor | 0/16 | 5/24 |
| Metastatic cerebral tumor | — | 6/6 |

ND: not determined.

Example 3

(Tumor Antigen Peptide Recognized by HLA-A24-restricted CTL)

In order to specify the tumor antigen peptide capable of binding to the HLA-A24 molecule, which is derived from Lck, thirteen different peptides were synthesized and loaded onto ClR/A2402 so as to test the ability of enhancing the IFN-γ production by KE4-CTLs.

With respect to peptides derived from Lck capable of binding to the HLA-A2402 molecule, peptides for HLA-A24-binding motif were search for in the literature, and thirteen peptides were synthesized based on the sequence of the lck gene product consisting of 509 amino acids (Nature, 319: 682-685, 1986), although some amino acids of some peptides were modified. The synthesized peptides are summarized in Table 2.

TABLE 2

| Lck peptide | Amino acid sequence | | | | | | | | | |
|---|---|---|---|---|---|---|---|---|---|---|
| 39-48 | R | N | G | S | E | Y | R | D | P | L (SEQ ID NO: 19) |
| 71-80 | S | Y | E | P | S | H | D | G | D | L (SEQ ID NO: 20) |
| 114-122 | N | F | V | A | K | A | N | S | L | (SEQ ID NO: 21) |
| 162-170 | S | F | S | L | S | V | R | D | F | (SEQ ID NO: 22) |
| 191-199 | F | Y | I | S | P | R | I | T | F | (SEQ ID NO: 23) |
| 208-216 | H | Y | T | N | A | S | D | G | L | (SEQ ID NO: 3) |
| 303-312 | L | Y | A | V | V | T | Q | E | P | I (SEQ ID NO: 24) |
| 317-325 | E | Y | M | E | N | G | S | L | V | (SEQ ID NO: 25) |
| 353-361 | A | F | I | E | E | R | N | Y | I | (SEQ ID NO: 26) |
| 393-402 | E | Y | T | A | R | E | G | A | K | F (SEQ ID NO: 27) |
| 445-453 | T | N | P | E | V | I | Q | N | L | (SEQ ID NO: 28) |
| 486-494 | T | F | D | Y | L | R | S | V | L | (SEQ ID NO: 1) |
| 488-497 | D | Y | L | R | S | V | L | E | D | F (SEQ ID NO: 2) |

In order to specify the tumor antigen, ClR/A2402 ($2\times10^4$) cells transfected with HLA-A2402 were pulsed with a peptide at a final concentration of 10 μM for 2 h. KE4-CTLs ($1\times10^4$) were then added, and incubated for 18 h. 100 μl of the supernatant was collected to measure IFN-γ by ELISA.

Figure 4:
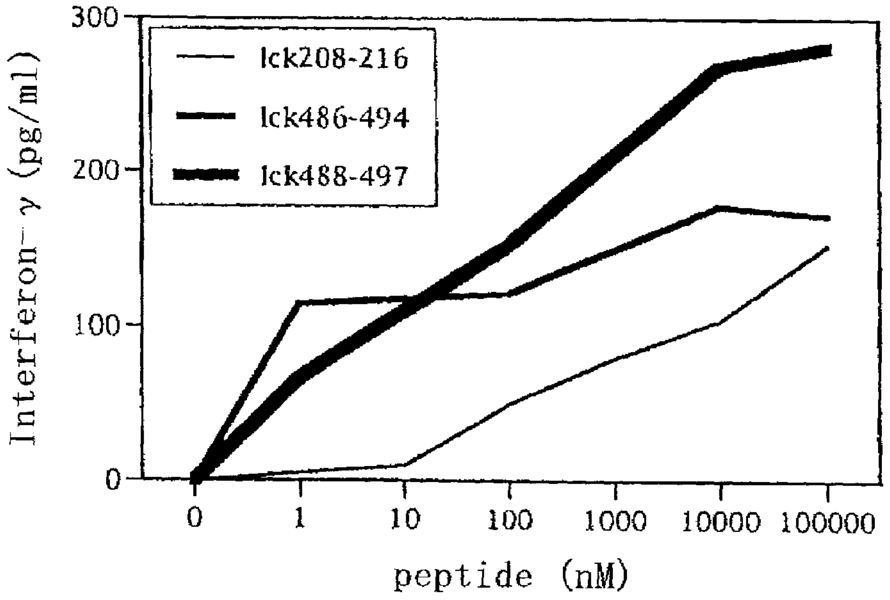
FIG. 4 illustrates the dose-dependent activation of KE-CTLs by the peptide derived from Lck.

Among 13 peptides synthesized, 6 peptides [Lck71-80, Lck208-216 (SEQ ID NO:3), Lck317-325, Lck353-361, Lck486-494 (SEQ ID NO:1), or Lck488-497 (SEQ ID NO:2)] had an activity of enhancing the IFN-γ production in CTLs (FIG. 3), and 3 peptides [Lck208-216 (SEQ ID NO:3), and Lck486-494 (SEQ ID NO:1), Lck488-497 (SEQ ID NO:2)] showed a strong activity. The activity of Lck486-494 (SEQ ID NO:1) or Lck488-497 (SEQ ID NO:2) peptide to enhance the IFN-γ production by CTLs proved to be dose-dependent, and was detected at 1 nM or so. On the other hand, the activity of Lck208-216 (SEQ ID NO:3) was detected at 100 nM or higher (FIG. 4).

Similar results were obtained also in the case where VA13 cells ($2\times10^4$) were used in place of ClR/A2402 cells, which were pulsed with these peptides after transfecting with HLA-A2402 to use as a stimulator.

Figure 5:
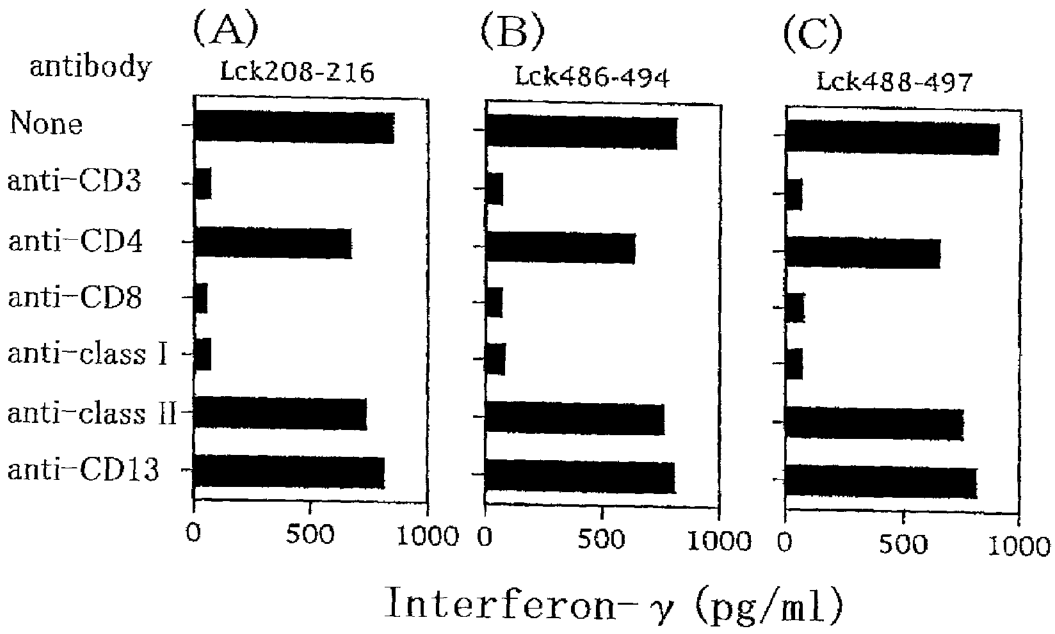
FIG. 5 illustrates the phenotype and MHC restriction of KE-CTLs confirmed by testing the recognition of the peptide by KE-CTLs in the presence of various antibodies. (A) Lck208-216 was used as a peptide derived from Lck. (B) Lck486-494 was used as a peptide derived from Lck. (C) Lck488-497 was used as a peptide derived from Lck.

When anti-CD3 (NuT3), anti-CD4 (NuTh/s), anti-CD8 (NuTc/i), anti-CD13 (MCS-2), anti-MHC class I (W6/32) or anti-MHC class II (HDR1) antibody (Int. J. Cancer, 58: 317-323, 1994) was used in the above-mentioned CTL activation test, IFN-γ production by KE4-CTL in the reaction against ClR/A2402 cells pulsed with each of three peptides was inhibited by anti-CD3, anti-CD8 and anti-MHC class I monoclonal antibody, but not by anti-CD4, anti-MHC class II and anti-CD13 monoclonal antibody [FIG. 5(A), (B) and (C)]. Therefore, it was confirmed that the KE4-CTL has the phenotype of $CD3^+$ $CD8^+$ $CD4^-$, and is a cytotoxic T lymphocyte that recognizes MHC class I.

In addition, in order to confirm peptide specificity in CTLs, sublines of KE4-CTL were established from the parental HLA-A2402-restricted KE4-CTL by the limiting dilution culture (J. Exp. Med. 187: 277-288, 1998). With respect to 20 different KE4-CTL sublines obtained having the phenotype of $CD3^+$ $CD8^+$ $CD4^-$, the reactivity against each of the above-mentioned three peptides was tested.

Figure 6:
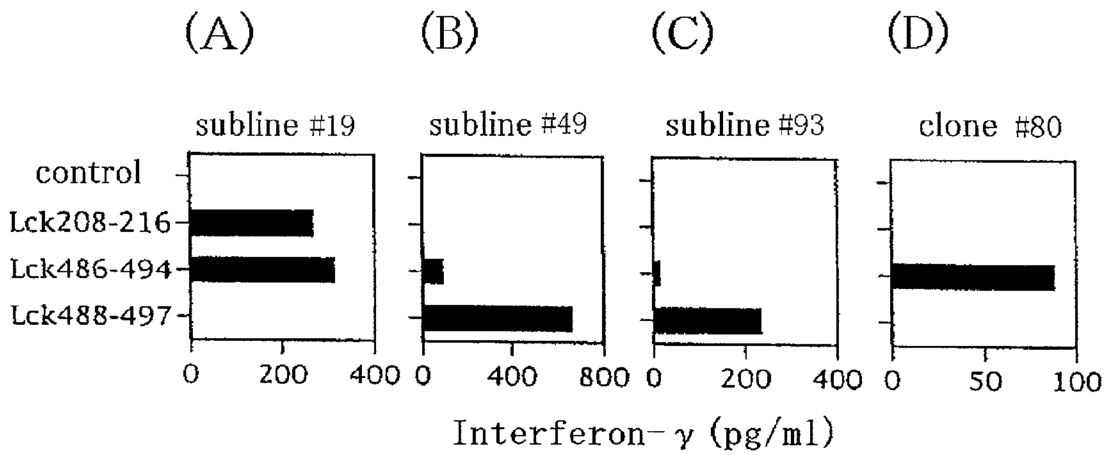
FIG. 6 illustrates the difference in the peptide recognition among KE4-CTL sublines. (A) Subline #19 was used. (B) Subline #49 was used. (C) Subline #93 was used. (D) Clone #80 was used.

As a result, two sublines (sublines #49 and #93) recognized Lck488-497 (SEQ ID NO:2), and one clone (clone #80) recognized Lck486-494 (SEQ ID NO:1) [FIGS. 6(B), (C) and (D)]. Subline #19 recognized both Lck208-216 (SEQ ID NO:3) and Lck486-494 (SEQ ID NO:1) [FIG. 6(A)]. Sixteen other sublines did not recognize any of these peptides. This result suggests that CTLs may be a population comprising cells that recognize a plural number of tumor antigens.

Example 4

(Induction of HLA-A24-restricted Cytotoxic T Cell by Peptide)

Activities of three peptides [Lck208-216 (SEQ ID NO:3), Lck486-494 (SEQ ID NO:1), and Lck488-497 (SEQ ID NO:2)] were tested with respect to inducing HLA-A24-restricted CTLs against tumor cell lines (KE4, W620 and COLO201) that is expressing Lck protein, from PBMCs obtained from a colon cancer patient.

PBMCs ($2\times10^6$) of an HLA-A24$^+$ patient or healthy donor were incubated with 10 μM of peptide in each well of a 24-well plate containing 2 ml of a culture medium (45% RPMI-1640 medium, 45% AIM-V® medium/GIBCO BRL, and 10% FCS with 100 U/ml of IL-2 and 0.1 mM MEM non-essential amino acid solution/GIBCO BRL).

At days 7 and 14 of culture, cells were collected, washed, and stimulated with autologous PBMCs or dendritic cells that were irradiated (50 Gray) and pulsed with the peptide as antigen-presenting cells (APCs). The dendritic cells were induced by incubating PBMCs ($2\times10^6$ cell/well) in RPMI1640 (GIBCO BRL) containing 10% FCS and 100 U/ml IL-4 and 100 U/ml GM-CSF (granulocyte macrophage-colony stimulating factor) for 7 days.

Figure 7:
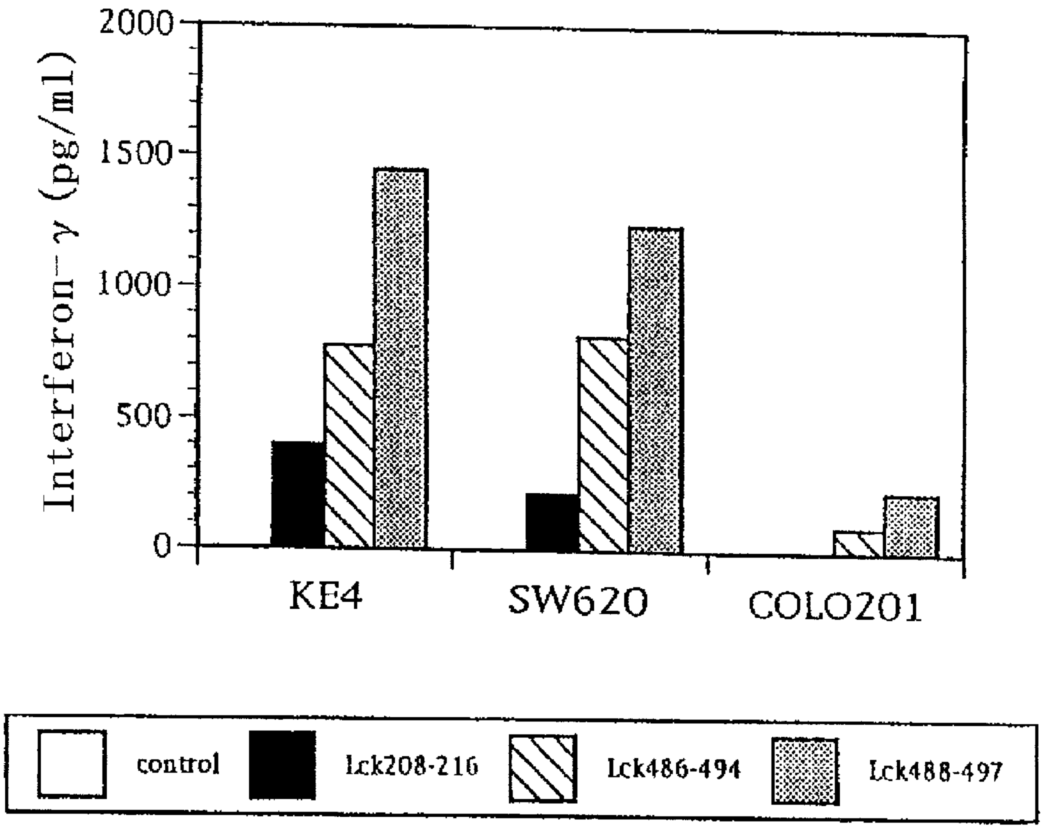
FIG. 7 illustrates that a peptide derived from Lck can induce HLA-A24-restricted cytotoxic T lymphocytes from peripheral blood mononuclear cells (PBMCs) of a cancer patient. The IFN-γ produced from CTLs was investigated as an indicator for the induction, using tumor cells such as KE-4 (HLA-A24$^+$), SW620 (HLA-A24$^+$), and COLO201 (HLA-A24$^-$) as target cells.

The cells collected at day 21 were immediately tested by the ELISA method on the reactivity as the effector to various target cells by using the ability of IFN-γ production as an index. The result is illustrated in FIG. 7. PBMCs stimulated in vitro three times with Lck208-216 (SEQ ID NO:3), Lck486-494 (SEQ ID NO:1), or Lck488-497 (SEQ ID NO:2), particularly PBMCs stimulated with Lck486-494 (SEQ ID NO:1) or Lck488-497 (SEQ ID NO:2) produced a greater amount of IFN-γ in the reaction to an HLA-A24$^+$ tumor cell (KE4 and SW620) than in the reaction to an HLA-A24$^-$ tumor cell (COLO201). On the other hand, PBMCs obtained from a healthy donor did not exhibit an HLA-A24-restricted CTL activity even if stimulated with any of the three peptides pulsed using irradiated PBMCs for antigen-presenting cells (APCs). PBMCs obtained from a healthy donor exhibited an HLA-A24-restricted CTL activity when stimulated using dendritic cells (DCs) pulsed with the peptide as APCs (Table 3).

TABLE 3

| Donor | Antigen-presenting cell | Peptide | Amount of interferon-γ. production by recognition of cancer cell line (pg/ml) KE4 (A24$^+$) | SW620 (A24$^+$) | COLO201 (A24$^-$) |
|---|---|---|---|---|---|
| Colon cancer patient | Autologous peripheral blood mono-nuclear cell | None | 1079 | 902 | 194 |
| | | Lck208-216 | 1479 | 1113 | 188 |
| | | Lck486-494 | 1857 | 1724 | 289 |
| | | Lck488-497 | 2527 | 2140 | 424 |
| Healthy donor 1 | Autologous dendritic cell | None | 230 | 380 | 54 |
| | | Lck208-216 | 570 | 786 | 124 |
| | | Lck486-494 | 1105 | 2061 | 177 |
| | | Lck488-497 | 621 | 966 | 122 |

TABLE 3-continued

| Donor | Antigen-presenting cell | Peptide | Amount of interferon-γ. production by recognition of cancer cell line (pg/ml) KE4 (A24$^+$) | SW620 (A24$^+$) | COLO201 (A24$^-$) |
|---|---|---|---|---|---|
| Healthy donor 2 | Autologous peripheral blood mono-nuclear cell | None | 101 | 187 | 0 |
| | | Lck208-216 | 82 | 128 | 1 |
| | | Lck486-494 | 41 | 94 | 10 |
| | | Lck488-497 | 90 | 140 | 6 |

Figure 8:
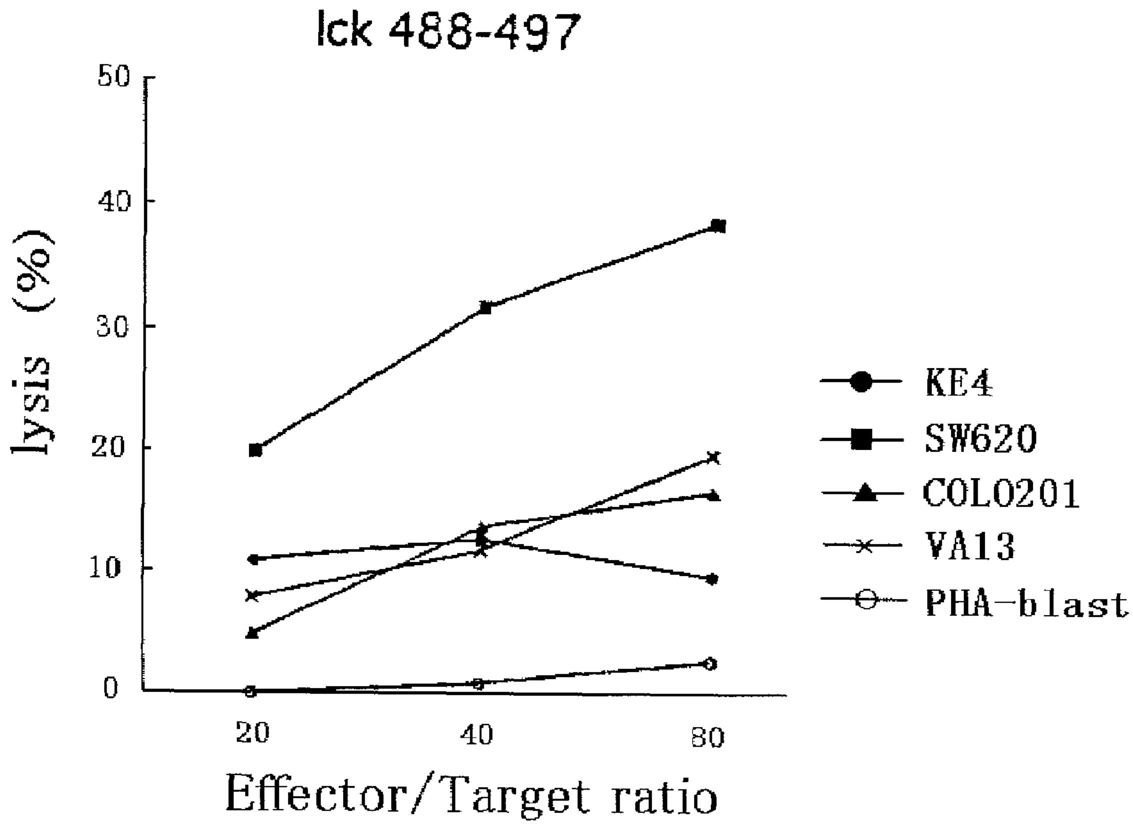
FIG. 8 illustrates the cytotoxic activity of CTLs induced by a peptide derived from Lck against various tumor cells. The activity was examined by the $^{51}$Cr-release test. (A) Lck488-497 was used as the peptide. (B) Lck208-216 was used as the peptide.
Figure 8:
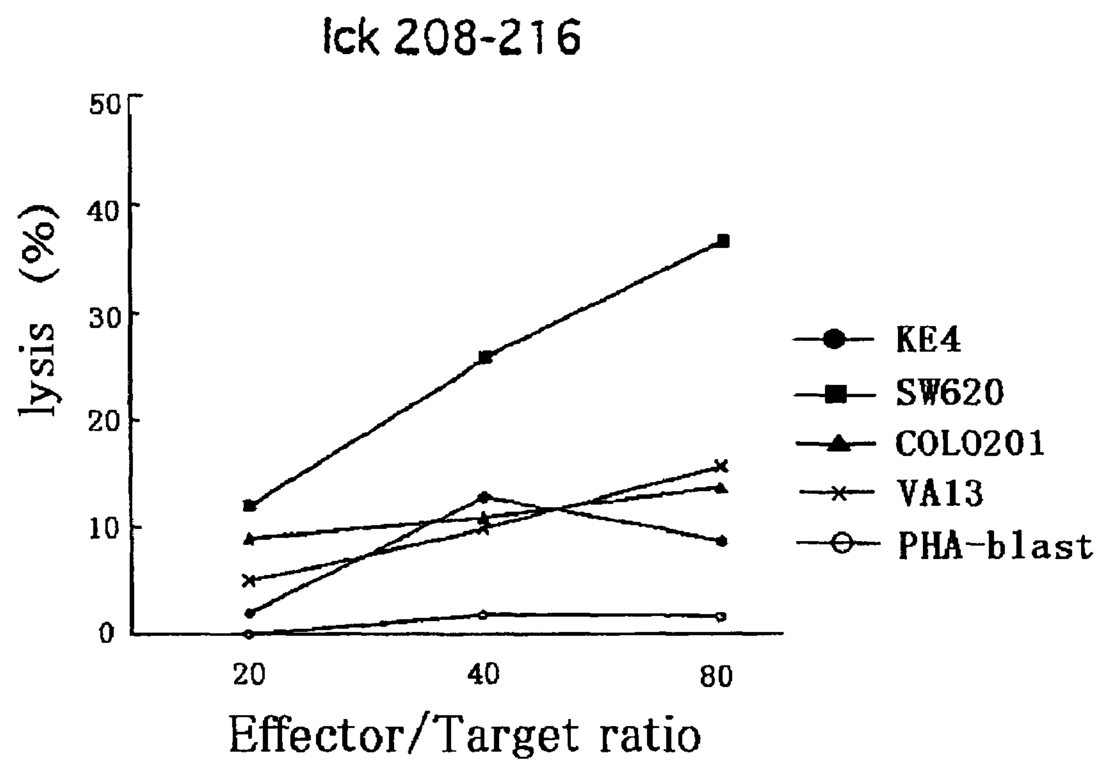

In addition, for the test of $^{51}$Cr release from target cells, the above-mentioned PBMCs that were stimulated three times with a peptide were further co-cultured with feeder cells consisting of irradiated HLA-A24$^+$ allogenic PBMCs ($2\times10^5$ cells/well) that had been pulsed with a corresponding peptide. At around day 24 of the re-culture, the cytotoxic T lymphocyte activity of these cells was confirmed by the assay of the IFN-γ production, and these cells were directly tested for their cytotoxicity by a 6 h $^{51}$Cr-release test at a various effector/target ratio. PBMCs stimulated with each of the above-mentioned three peptides derived from Lck lysed HLA-A24$^+$ KE tumor cells and SW620 tumor cells, but did not lyse either HLA-A24$^+$ PHA-activated T lymphocytes from a healthy donor or HLA-A24$^-$ COLO201 tumor cells. Results with Lck488-497 are illustrated in FIG. 8(A), and those with Lck208-216 in FIG. 8(B). Thus, a peptide derived from Lck proved to be able to induce HLA-A24-restricted and tumor-specific cytotoxic T lymphocytes.

Example 5

(Induction of HLA-A24-restricted CTL in Peripheral Blood Mononuclear Cells Obtained From a Cancer Patient)

With respect to three peptides [Lck208-216 (SEQ ID NO:3), Lck486-494 (SEQ ID NO:1), and Lck488-497 (SEQ ID NO:2)], the activity of inducing HLA-A24-restricted CTL against Lck-expressing tumor cell lines (KE4, SW620 and COLO201) from PBMCs obtained from a cancer patient was assayed using the amount of INF-γ production as an indicator. The method for inducing CTLs and the method for assaying IFN-γ were similar to those used in Example 4.

As a result, as shown in Table 4, CTLs were induced by Lck208-216 (SEQ ID NO:3) and Lck488-497 (SEQ ID NO:2) from PBMCs of a colon cancer patient and an esophageal cancer patient.

TABLE 4

| Case | Age | Sex | Cancer species | Presence or absence of metastasis | CTL induction by Lck peptide: No peptide | Lck 208-216 | Lck 486-494 | Lck 488-497 |
|---|---|---|---|---|---|---|---|---|
| N.I. | 51 | Male | Colon | + | − | + | − | + |
| Y.K. | 73 | Female | Esophageal | + | Not determined | + | − | + |

Figure 9:
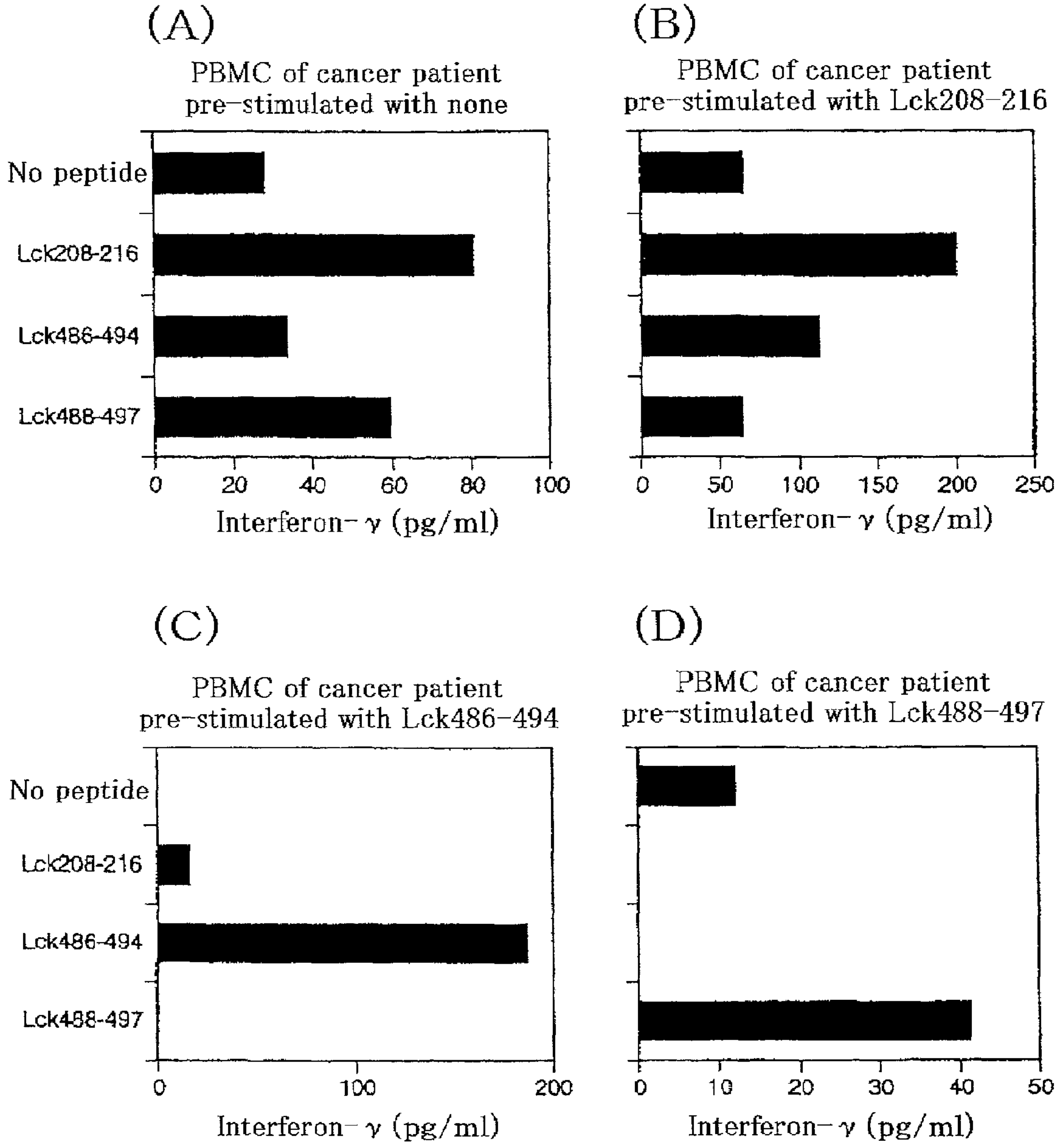
FIG. 9 illustrates the specificity of CTLs induced by a peptide from peripheral blood mononuclear cells (PBMCs) of a colon cancer patient against the peptide. (A) Any peptide was not used in the preliminary stimulation of PBMCs of a cancer patient. (B) Lck208-216 was used as the peptide in the preliminary stimulation of PBMCs of a cancer patient. (C) Lck486-494 was used as the peptide in the preliminary stimulation of PBMCs of a cancer patient. (D) Lck488-497 was used as the peptide in the preliminary stimulation of PBMCs of a cancer patient.

Next, PBMCs ($2\times10^6$) of the colon cancer patient were previously stimulated by adding three peptides, i.e., Lck208-216 (SEQ ID NO:3), Lck486-494 (SEQ ID NO:1), or Lck488-497 (SEQ ID NO:2), and further cultured after adding to HLA-A24$^+$ ClR/A2402 cells incubated with 10 μg/ml of each peptide for antigen-presenting, and the amount of INF-γ produced in the culture supernatant was assayed. As shown in FIGS. 9(A), (B), (C) and (D), PBMCs of a colon cancer patient that had been previously stimulated with Lck486-494 (SEQ ID NO:1) or Lck488-497 (SEQ ID NO:2) reacted only to peptides presented by antigen-presenting cells, i.e., Lck486-494 (SEQ ID NO:1) or Lck488-497 (SEQ ID NO:2) respectively to produce IFN-γ, i.e., to induce CTLs. Namely, Lck486-494 (SEQ ID NO:1) or Lck488-497 (SEQ ID NO:2) proved to be able to induce peptide-specific CTLs from PBMCs of a colon cancer patient by the pre-stimulation. On the other hand, when PBMCs of a colon cancer patient were previously stimulated by Lck208-216 (SEQ ID NO:3), or in the absence of the peptide, peptide-specific CTLs could not be induced.

Figure 10:
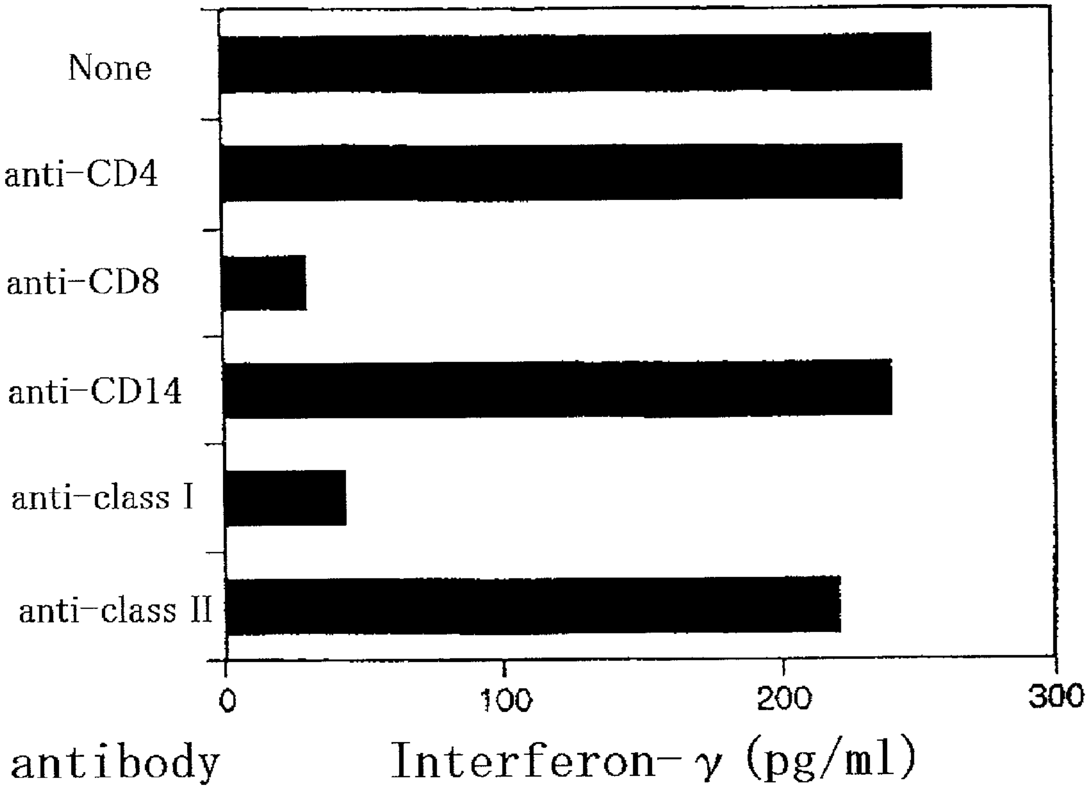
FIG. 10 illustrates the phenotype and the MHC restriction of induced CTLs confirmed by investigating the induction of the CTLs from peripheral blood mononuclear cells (PBMCs) of a colon cancer patient by a peptide in the presence of each of various antibodies.

Then, in order to examine the properties of CTLs induced from the colon cancer patient, using the SW620 cell as a target cell, 10 μg/ml of anti-CD4 (NuTh/s), anti-CD-8 (NuTc/i), anti-CD14, anti-MHC class I (W6/32) or anti-MHC class II (HDR1) antibody and 10 μg/ml of Lck488-497 (SEQ ID NO:2) were added, followed by incubation with CTLs induced from the colon cancer patient and the amount of IFN-γ produced in the supernatant was determined (FIG. 10). As a result, the production of IFN-γ from CTLs was inhibited by anti-CD8 and anti-MHC class I monoclonal antibody. Therefore, CTLs induced from a colon cancer patient were confirmed to be cytotoxic T lymphocytes that have the phenotype CD8$^+$ CD4$^-$ and recognize MHC class I.

Figure 11:
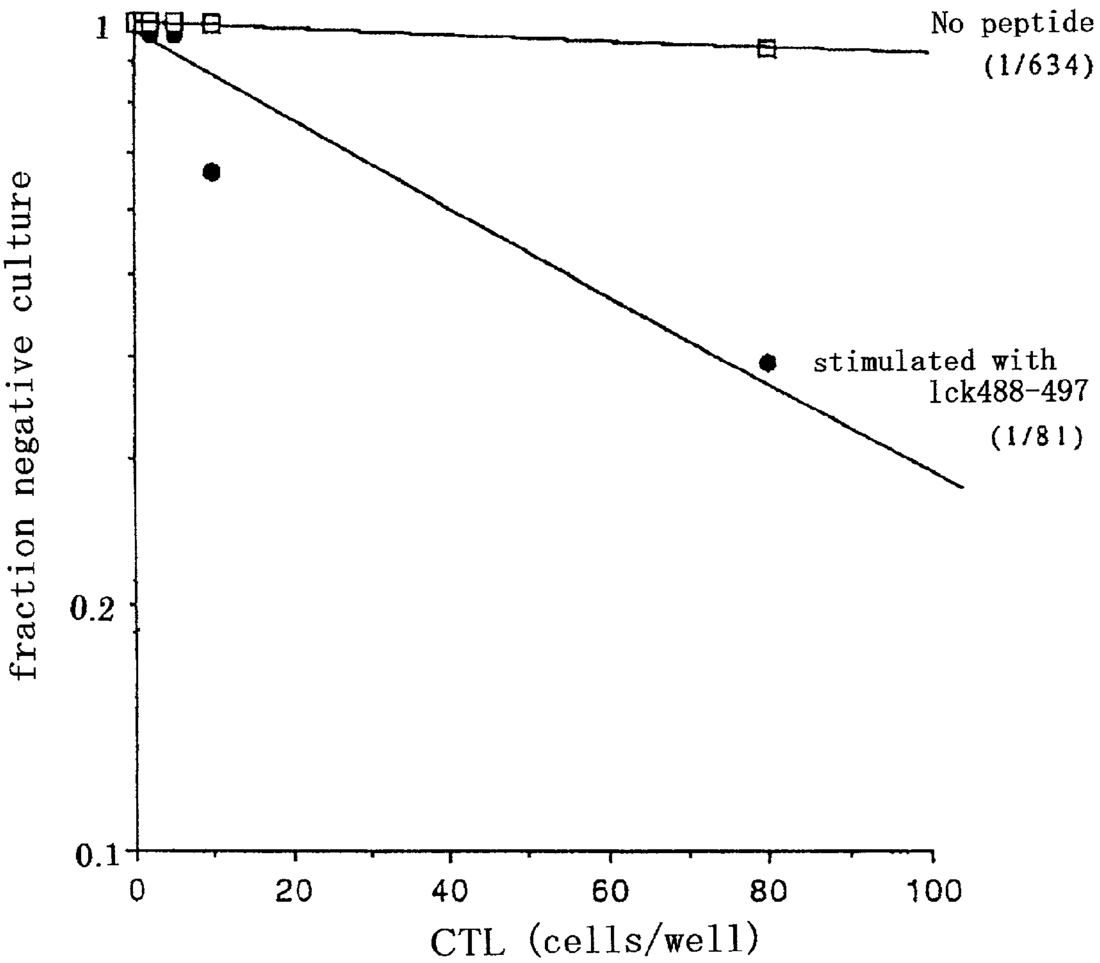
FIG. 11 illustrates the frequency of CTL precursor cells induced by a peptide in peripheral blood mononuclear cells (PBMCs) of a colon cancer patient. The abscissa indicates the number of CTLs added per well. The ordinate indicates the fraction of negative culture. With respect to the ordinate, "1" indicates that CTLs are not induced, so that 100% of target cells to be lysed by CTLs survived, "0.2" indicates that all the target cells were killed (CTL precursor cell frequency=1/96).

CTL precursor cells in PBMCs of the above-mentioned colon cancer patient were examined. SW620 cells were placed in a 96-well plate for incubation, and 1-100 CTL(s) of the above-mentioned colon cancer patient that had been previously stimulated by Lck488-497 (SEQ ID NO:2) was/were added to each well for further incubation, and a well was determined in which SW620 cells that are target cells survived. As a control, CTLs of the above-mentioned colon cancer patient that was not stimulated with the peptide were used. Results are illustrated in FIG. 11. The frequency of CTL precursor cells in PBMCs of the colon cancer patient was 1/634 when not stimulated with the peptide, but was 1/81 when stimulated with Lck488-497 (SEQ ID NO:2). Therefore, it was confirmed that the number of CTL precursor cells is increased by stimulation with the peptide.

Example 6

(Examination of Peptide Having HLA-A24-restricted CTL-Inducing Property)

Thus, three peptides derived from Lck, i.e., Lck208-216 (SEQ ID NO:3) (HYTNASDGL), Lck486-494 (SEQ ID NO:1) (TFDYLRSVL) and Lck488-497 (SEQ ID NO:2) (DYLRSVLEDF) were found to be able to induce CTLs that recognize HLA-A24$^+$ tumor cell line. These results suggest that the amino acid sequence DYLRSV (SEQ ID NO:46), which is the overlapping region for the two peptides Lck486-494 (SEQ ID NO:1) and Lck488-497 (SEQ ID NO:2), is recognized as a tumor antigen epitope by CTLs induced by the peptide, and that this part included in the kinase domain of Lck protein has a relevance to tumor rejection. With attention to this amino acid sequence DYLRSV (SEQ ID NO:46), peptides that are homologous to this sequence were searched for, so that such peptides were found to be included in the amino acid sequence of some tyrosine kinases (Ann. Rev. Biochem. 54: 897-930, 1985) which are belonging to the Src family as well as Lck, as shown in Table 5.

TABLE 5

| | | | | | | | | | | | | | |
|---|---|---|---|---|---|---|---|---|---|---|---|---|---|
| | | | 488-497 | | | | | | | | | | |
| (SEQ. ID. NO. 47) Lck 486-498 | T | F | D | Y | L | R | S | V | L | E | D | F | F |
| | 486-494 | | | | | | | | | | | | |
| (SEQ. ID. NO. 48) Src 511-523 | T | F | E | Y | L | Q | A | F | L | E | D | Y | F |
| (SEQ. ID. NO. 49) Yes 508-520 | T | F | E | Y | I | Q | S | F | L | E | D | Y | F |
| (SEQ. ID. NO. 50) Fgr 504-516 | T | F | E | Y | L | Q | S | F | L | E | D | F | F |
| (SEQ. ID. NO. 51) Fyn 512-524 | T | F | E | Y | L | Q | S | F | L | E | D | Y | F |
| (SEQ. ID. NO. 52) Lyn 489-501 | T | F | D | Y | L | Q | S | V | L | D | D | F | Y |
| (SEQ. ID. NO. 53) Hck 503-515 | T | F | E | Y | I | Q | S | V | L | D | D | F | Y |
| (SEQ. ID. NO. 54) Blk 482-494 | T | F | E | F | L | Q | S | V | L | E | D | F | Y |

Figure 12:
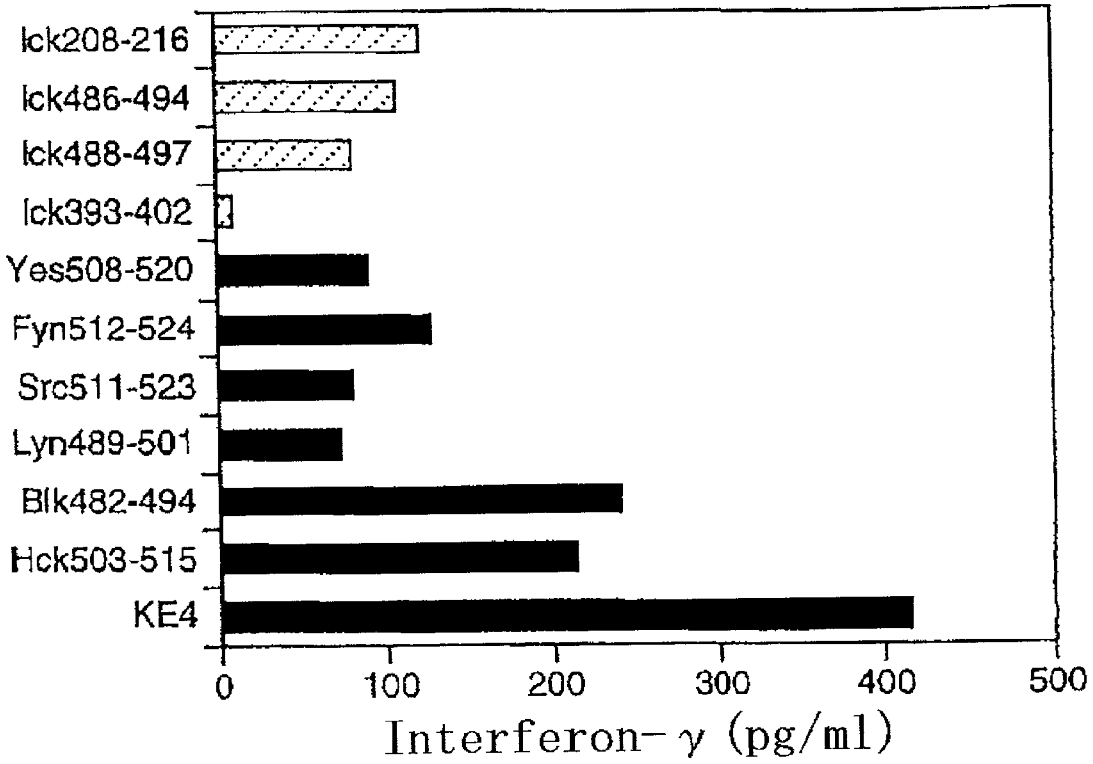
FIG. 12 illustrates the activation of KE4-CTLs by a peptide derived from Src family.

Based on these amino acid sequences of the peptides derived from Src family, Src511-519 (SEQ ID NO:4) (TFEYLQAFL), Yes508-516 (SEQ ID NO:5) (TFEYIQSFL), Fyn512-520 (SEQ ID NO:6) (TFEYLQSFL), Lyn489-497 (SEQ ID NO:7) (TFDYLQSVL), Hck503-511 (SEQ ID NO:8) (TFEYIQSVL), and Blk482-490 (SEQ ID NO:9) (TFEFLQSVL) were synthesized, and 10 μg/ml of each peptide was incubated with SW620 cells used as target cells, and then KE4-CTL cells used in Examples 1 and 2 were added and then cultured to assay a CTL-inducing activity using the amount of IFN-γ produced in the culture supernatant as the indicator. In addition, KE4 as a positive control was used for the target cell. Other methods were similar to those used in Example 4. As shown in FIG. 12, each peptide derived from the Src family showed a CTL-inducing ability comparable or greater to the peptide derived from Lck.

Example 7

(Induction of CTL by Peptide Derived From Src Family in a Cancer Patient)

With respect to Lck486-494 (SEQ ID NO:1) (TFDYLRSVL), Src511-519 (SEQ ID NO:4) (TFEYLQAFL), Yes508-516 (SEQ ID NO:5) (TFEYIQSFL), Fyn512-520 (SEQ ID NO:6) (TFEYLQSFL), Lyn489-497 (SEQ ID NO:7) (TFDYLQSVL), Hck503-511 (SEQ ID NO:8) (TFEYIQSVL), and Blk482-490 (SEQ ID NO:9) (TFEFLQSVL), induction of HLA-A24-restricted CTLs from PBMCs obtained from a metastatic cancer patient was examined. The induction of CTLs and the assay of CTL activity were carried out in manners similar to those used in Example 4, and KE4 cells (HLA-A2402/26), SW620 cells (HLA-A0201/24), COLO201 cells (HLA-A0101/0201), and VA13 cells (HLA-A02) were used as target cells. CTLs were induced in PBMCs by Lck486-494 (SEQ ID NO:1) in 4 cases among 7 cases of cancer patients, by Src511-519 (SEQ ID NO:4) in 2 cases among 3 cases, by Yes508-516 (SEQ ID NO:5) in 1 case among 3 cases, by Fyn512-520 (SEQ ID NO:6) in 1 case among 2 cases, by Hck503-511 (SEQ ID NO:8) in 2 cases among 2 cases, and by Blk482-490 (SEQ ID NO:9) in 1 case among 2 cases. However, CTLs were not induced by Lyn489-497 in each of 2 cases tested.

Example 8

(Tumor Antigen Peptide Recognized by HLA-A2-restricted CTL)

In order to specify an HLA-A2 molecule-binding tumor antigen peptide derived from Lck, 24 different peptides were synthesized to introduce into VA 13 (HLA-A02), and an ability of enhancing INF-γ production by OK-CTL or GK-CTL subline (2-2-4) was tested in a manner similar to one used in Example 3.

Peptides derived from Lck capable of binding to the HLA-A2 molecule were prepared by searching for peptides for HLA-A2-binding motif, followed by synthesizing 24 different peptides based on the sequence of the lck gene product consisting of 509 amino acids (Nature, 319: 682-685, 1986). Synthesized peptides are summarized in Tables 6 and 7.

TABLE 6

HLA-A0201-binding motif of peptides derived from Lck

| | | | | | | | | | | |
|---|---|---|---|---|---|---|---|---|---|---|
| 340-348 | K | L | L | D | M | A | A | Q | I | (SEQ ID NO: 14) |
| 185-193 | N | L | D | N | G | G | F | Y | I | (SEQ ID NO: 29) |
| 36-44 | L | L | I | R | N | G | S | E | V | (SEQ ID NO: 30) |
| 387-395 | R | L | I | E | D | N | E | Y | T | (SEQ ID NO: 31) |
| 347-355 | Q | I | A | E | G | M | A | F | I | (SEQ ID NO: 15) |
| 492-500 | S | V | L | E | D | F | F | T | A | (SEQ ID NO: 17) |
| 299-307 | R | L | V | R | L | Y | A | V | V | (SEQ ID NO: 32) |
| 493-501 | V | L | E | D | F | F | T | A | T | (SEQ ID NO: 33) |

TABLE 6-continued

HLA-A0201-binding motif of peptides derived from Lck

| | | | | | | | | | | | |
|---|---|---|---|---|---|---|---|---|---|---|---|
| 246-254 | K | L | V | E | R | L | G | A | A | | (SEQ ID NO: 12) |
| 279-287 | S | M | S | P | D | A | F | L | A | | (SEQ ID NO: 34) |
| 293-301 | K | Q | L | Q | H | Q | R | L | V | | (SEQ ID NO: 35) |
| 151-159 | F | L | I | R | E | S | E | S | T | | (SEQ ID NO: 36) |
| 35-44 | R | L | L | I | R | N | G | S | E | V | (SEQ ID NO: 37) |
| 201-210 | G | L | H | E | L | V | R | H | Y | T | (SEQ ID NO: 38) |
| 231-240 | K | P | W | W | E | D | E | W | E | V | (SEQ ID NO: 39) |
| 379-388 | K | I | A | D | F | G | L | A | R | L | (SEQ ID NO: 40) |
| 294-303 | Q | L | Q | H | Q | R | L | V | R | L | (SEQ ID NO: 13) |
| 335-344 | K | L | T | T | N | K | L | L | D | M | (SEQ ID NO: 41) |
| 110-119 | F | I | P | F | N | F | V | A | K | A | (SEQ ID NO: 42) |
| 250-259 | R | L | G | A | A | Q | F | G | E | V | (SEQ ID NO: 43) |

TABLE 7

HLA-A0206-binding motif of peptides derived from Lck

| | | | | | | | | | | | |
|---|---|---|---|---|---|---|---|---|---|---|---|
| 61-69 | L | Q | D | N | L | V | I | A | L | | (SEQ ID NO: 11) |
| 239-247 | E | V | P | R | E | T | L | K | L | | (SEQ ID NO: 44) |
| 422-430 | D | V | W | S | F | G | I | L | L | | (SEQ ID NO: 16) |
| 27-36 | I | V | R | L | D | G | K | D | R | L | (SEQ ID NO: 45) |

In order to specify the tumor antigen peptide, $2\times10^4$ of VA13 cells transfected with HLA-A2 were pulsed with the peptide at a final concentration of 10 μM for 2 h. $1\times10^4$ of KE4-CTLs were then added and incubated for 18 h. 100 μl of the supernatant was collected to measure IFN-γ by ELISA.

Among these peptides, seven peptides [Lck61-69 (SEQ ID NO:11), Lck246-254 (SEQ ID NO:12), Lck294-303 (SEQ ID NO:13), Lck340-348 (SEQ ID NO:14), Lck347-355 (SEQ ID NO:15), Lck422-430 (SEQ ID NO:16), or Lck492-500 (SEQ ID NO:17)] enhanced the production of IFN-γ by OK-CTL subline and GK-CTL subline (2-2-4) [FIG. 13(A) and (B)]. When a similar experiment was carried out at various concentrations of the peptide to pulse, Lck61-69 (SEQ ID NO:11) activated particularly OK-CTL subline, and Lck246-254 (SEQ ID NO:12) activated particularly GK-CTL subline (2-2-4), and Lck422-430 (SEQ ID NO:16) activated particularly GK-CTL subline (2-2-5), in a dose-dependent manner, to enhance the production of IFN-γ from these CTLs [FIGS. 14(A), (B), and (C)].

Example 9

(Induction of HLA-A2-restricted Cytotoxic T Lymphocyte by Peptide)

With respect to three peptides [Lck61-69 (SEQ ID NO:11), Lck246-254 (SEQ ID NO:12), or Lck422-430 (SEQ ID NO:16)], the activity was examined of inducing HLA-A2-restricted CTLs against tumor cell lines Panc-1, SW620, COLO320 and VA13 from PBMCs obtained from a metastatic colon cancer patient.

Using PBMCs of a metastatic HLA-A2$^+$ colon cancer patient, the induction of CTLs and the assay of IFN-γ were carried out in manners similar to those used in Example 4 [FIGS. 15(A) and (C)]. In addition, the cytotoxic activity of the CTLs was directly assayed by the $^{51}$Cr-release test [FIGS. 15(B) and (D)]. Lck246-254 (SEQ ID NO:12) and Lck422-430 (SEQ ID NO:16) induced HLA-A2-restricted and tumor-specific CTLs from PBMCs obtained from a metastatic HLA-A2$^+$ colon cancer patient.

Example 10

(Induction of HLA-A2-restricted CTL in a Cancer Patient)

The ability of three peptides [Lck61-69 (SEQ ID NO:11), Lck246-254 (SEQ ID NO:12), or Lck422-430 (SEQ ID NO:16)] to induce HLA-A2-restricted CTLs from PBMCs obtained from various cancer patients was studied. The induction of CTLs and the assay of CTL activity were carried out in manners similar to those used in Example 4, using SW620 cells (HLA-A0201/24) as target cells. CTLs were induced in PBMCs by Lck246-254 (SEQ ID NO:12, 2 cases among 6 cases) and Lck422-430 (SEQ ID NO:16, 3 cases among 6 cases) (Table 8).

TABLE 8

| | | | | | | CTL induction by Lck peptide | | | |
|---|---|---|---|---|---|---|---|---|---|
| Case | Age | Sex | Cancer species | Stage | Metastasis | No peptide | Lck 246-254 | Lck 61-69 | Lck 422-430 |
| 1 | 53 | Female | Colon cancer | IV | + | − | + | − | − |
| 2 | 72 | Female | Colon cancer | IV | + | − | + | − | + |
| 3 | 57 | Female | Colon cancer | IIIa | + | − | − | − | − |
| 4 | 76 | Male | Pulmonary cancer | III | + | − | − | − | + |
| 5 | 50 | Male | Esophageal cancer | IV | + | − | − | − | + |
| 6 | 73 | Male | Gastric cancer | I | − | − | − | − | − |

INDUSTRIAL APPLICABILITY

Peptides derived from Lck and peptides derived from the Src family, according to the present invention, are tumor antigen peptides, and can induce HLA-A24-restricted and/or HLA-A2-restricted and tumor-specific cytotoxic T lymphocytes from PBMCs of a cancer patient. Lck proteins are expressed in a majority of cancer tissues including large intestine, lung and esophagus. Namely, tumor antigen peptides according to the present invention can be used for the specific immunotherapy for cancer. In addition, the HLA-A24 allele is detected in approximately 60% of the Japanese population (in a majority, equal to 95%, the genotype is A2402), 20% of Caucasians, and 12% of Africans. The HLA-A2 allele is detected in approximately 40% of Japanese, 53% of Chinese, 49% of North Caucasians, 38% of South Caucasians, and 23% of Black Africans. Therefore, the specific immunotherapy using tumor antigen peptides according to the present invention can be used in many cancer patients. A peptide provided by the present invention can be used in many cancer patients. A peptide provided by the present invention, a polynucleotide encoding the peptide, and an antibody recognizing the peptide provide extremely useful means in the field of the treatment and diagnosis of cancers.

FREE TEXT IN SEQUENCE LISTING

SEQ ID NO:10;

<220>

<230> Designed peptide based on amino acid sequence of Src family tyrosine kinases, which peptide has an ability to generate HLA-A24 restricted cytotoxic T lymphocytes

<222> (3)

<230> Xaa can be Asp or Glu.

<222> (4)

<230> Xaa can be Tyr or Phe.

<222> (5)

<230> Xaa can be Leu or Ile.

<222> (6)

<230> Xaa can be Arg or Gln.

<222> (7)

<230> Xaa can be Ser or Ala.

<222> (8)

<230> Xaa can be Val or Phe.

<222> (10)

<230> Xaa can be Glu or Asp.

<222> (12)

<230> Xaa can be Phe or Tyr.

<222> (13)

<230> Xaa can be Phe or Tyr.

What is claimed is:

1. A peptide consisting of SEQ ID No:1, 2 or 3.

2. A tumor antigen, wherein the tumor antigen consists of a peptide of claim 1.

3. A composition comprising at least one peptide selected from a peptide of claim 1.

* * * * *